US009367822B2

(12) United States Patent
Shipon

(10) Patent No.: US 9,367,822 B2
(45) Date of Patent: Jun. 14, 2016

(54) SUPERVISION AND DATA CYBER SUPERHIGHWAY SYSTEM, METHOD AND MEDIUM

(76) Inventor: Jacob A. Shipon, Rydal, PA (US)

(*) Notice: Subject to any disclaimer, the term of this patent is extended or adjusted under 35 U.S.C. 154(b) by 134 days.

(21) Appl. No.: 13/560,232

(22) Filed: Jul. 27, 2012

(65) Prior Publication Data

US 2012/0293597 A1 Nov. 22, 2012

Related U.S. Application Data

(63) Continuation of application No. 11/359,289, filed on Feb. 22, 2006, now abandoned, which is a continuation-in-part of application No. 10/096,524, filed on Mar. 11, 2002, now abandoned.

(60) Provisional application No. 60/274,529, filed on Mar. 9, 2001.

(51) Int. Cl.
*G06Q 10/00* (2012.01)
*G06F 19/00* (2011.01)
*G06Q 30/06* (2012.01)
*G06Q 50/22* (2012.01)

(52) U.S. Cl.
CPC ............ *G06Q 10/00* (2013.01); *G06F 19/3418* (2013.01); *G06Q 30/06* (2013.01); *G06Q 50/22* (2013.01); *G06F 19/345* (2013.01)

(58) Field of Classification Search
CPC .................................................. G06F 19/3418
USPC .......................................................... 705/1.1
See application file for complete search history.

(56) References Cited

U.S. PATENT DOCUMENTS

| | | | |
|---|---|---|---|
| 5,434,611 A | | 7/1995 | Tamura |
| 5,441,047 A | * | 8/1995 | David et al. .................. 600/483 |
| 5,462,051 A | | 10/1995 | Oka et al. |
| 5,553,609 A | * | 9/1996 | Chen et al. .................... 600/301 |
| 5,619,991 A | | 4/1997 | Sloane |
| 5,748,907 A | | 5/1998 | Crane |

(Continued)

FOREIGN PATENT DOCUMENTS

WO WO 03/036439 5/2003

OTHER PUBLICATIONS

Derfler et al., "How Networks Work", 2003.*

(Continued)

*Primary Examiner* — Carrie S Gilkey
(74) *Attorney, Agent, or Firm* — Fish & Richardson P.C.

(57) ABSTRACT

A method provides supervision which includes providing a plurality of information channels for communicating information to the service provider and the user and integrating the information channels to provide access to supervisory functionality for supervising the information channels of the plurality of information channels by way of a single portal. The method provides access to audio/visual functionality, to information record functionality, to diagnostic functionality, to action functionality and to administrative functionality. All functionalities are accessed by way of a portal whereby the portal has access to the functionalities simultaneously. A single accessing of the portal by the user permits the user to gain access to all of the functionalities simultaneously in accordance with the single accessing. The portal can be a web portal. Each of the functionalities is accessed by way of a respective information channel of a plurality of information channels.

12 Claims, 12 Drawing Sheets

(56) References Cited

U.S. PATENT DOCUMENTS

| | | | |
|---|---|---|---|
| 5,810,747 A * | 9/1998 | Brudny et al. | 600/595 |
| 5,924,074 A | 7/1999 | Evans | |
| 5,987,510 A | 11/1999 | Imai et al. | |
| 6,046,761 A * | 4/2000 | Echerer | 348/14.01 |
| 6,223,165 B1 | 4/2001 | Lauffer | |
| 6,523,010 B2 | 2/2003 | Lauffer | |
| 6,638,218 B2 | 10/2003 | Bulat | |
| 6,731,324 B2 | 5/2004 | Levy | |
| 6,742,895 B2 | 6/2004 | Robin | |
| 6,781,982 B1 * | 8/2004 | Borella et al. | 370/352 |
| 6,795,554 B2 | 9/2004 | Farkas et al. | |
| 6,804,656 B1 | 10/2004 | Rosenfeld et al. | |
| 6,816,603 B2 | 11/2004 | David et al. | |
| 6,850,889 B1 | 2/2005 | Zayas, Jr. | |
| 6,908,431 B2 | 6/2005 | Bardy | |
| 7,011,629 B2 | 3/2006 | Bulat | |
| 7,038,588 B2 | 5/2006 | Boone et al. | |
| 2002/0022975 A1 | 2/2002 | Blasingame et al. | |
| 2002/0029350 A1 * | 3/2002 | Cooper et al. | 713/200 |
| 2002/0065682 A1 * | 5/2002 | Goldenberg | 705/2 |
| 2002/0065685 A1 | 5/2002 | Sasaki et al. | |
| 2003/0023459 A1 | 1/2003 | Shipon | |
| 2004/0221001 A1 * | 11/2004 | Anagol-Subbarao et al. | 709/203 |
| 2005/0073964 A1 * | 4/2005 | Schmidt et al. | 370/260 |
| 2006/0276179 A1 * | 12/2006 | Ghaffari et al. | 455/412.2 |

OTHER PUBLICATIONS

International Search Report for related PCT Application No. PCT/US07/62391, dated Nov. 8, 2007.

* cited by examiner

FIG. 9

Channel One
One On One Audio Visual-
Patient Supervsion
Computer/PDA/Video Phone/Video/
Kiosk Systems
& Component Options Channel Five
Clinical Trial Systems
Billing Management Systems
Claims Management Systems
Coordination Of Benefits
Payment Systems
Treatment & Benefit Audit
Special Purpose Software Packages
Distance Learning & Training
Dictation Transcription Services
Research Services
Group Conferencing Services
Customer Service Management
Medical Supply Services
Enterprise Platform Hosting
Intregration Services Channel Two
Virtual Electronic Records
Electronic Medical Records-
Managememt Systems
Medical Data Management
Image Transfer & Storage Systems
Data Intelligent Analysis System
Security Systems
Content Channel Three
Cardiac Monitoring Services
Monitor Systems Packages
Diagnostic Data Base Analytics Channel Four
Pharmacy Services
Pharmacology Data & Detailing
Lab Services
Set-up/Install/Training services

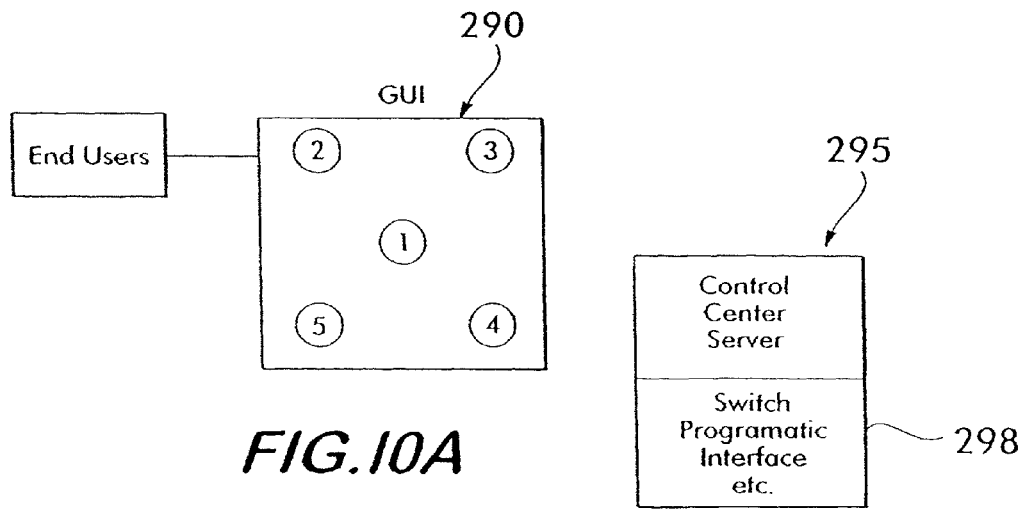

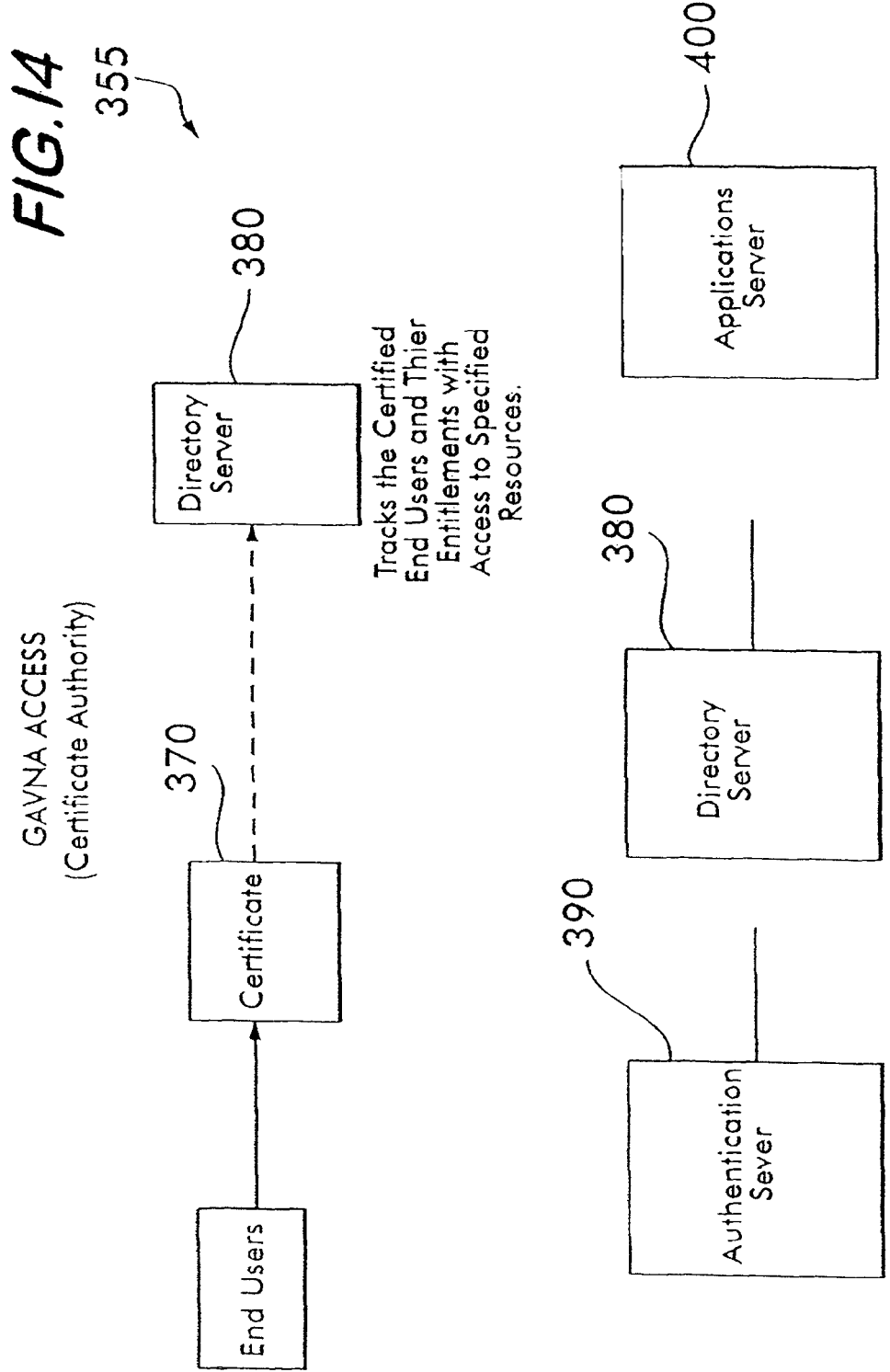

SUPERVISION AND DATA CYBER SUPERHIGHWAY SYSTEM, METHOD AND MEDIUM

CROSS-REFERENCE TO RELATED APPLICATIONS

This application claims the benefit under 35 U.S.C. §120 of U.S. application Ser. No. 11/359,289 filed on Feb. 22, 2006 which in turn is a continuation-in-part application that claims the benefit under 35 U.S.C. §120 of U.S. patent application Ser. No. 10/096,524, filed Mar. 11, 2002, which in turn claims the benefit under 35 U.S.C. §119(e) of Provisional U.S. Application Ser. No. 60/274,529 filed Mar. 9, 2001, and all of whose entire disclosures are incorporated by reference herein.

BACKGROUND OF THE INVENTION

1. Field of Invention

The present invention is directed to a method and system for teleconferencing to permit a service provider to provide a service to a user at a remote location.

2. Description of Related Art

The field of providing services from a service provider to users at locations remote from the location of the service provider by way of telecommunications systems such as the internet is a large and growing field. Using telecommunications systems in this manner allows the service provider and the user to interact easily from any distance at almost any time. Very importantly, systems such as these could permit unlimited resources to be applied to the interaction.

An important example of the fields of art where service providers can provide their services to users at remote locations is the health care industry. Recent research has established that the health care industry will achieve approximately $370 billion in online transactions by 2004, according to a report from Forrester Research. This report, entitled "Sizing Health Care E-Commerce," predicts that the Internet will become the foundation for a new health care industry infrastructure supporting complex, multiparty transactions among consumers, providers, insurers and medical suppliers. With 31% of online consumers already shopping for health care products on the web, online health sales and usage show no sign of slowing. There has already been a well documented growth and proliferation of online websites and medical related portals. The websites WebMD.com and DRKoop.com are examples of only two of the many such websites and portals.

Further, "Cyber Citizen Health", an ongoing program of research conducted by Cyber Dialogue published a study indicating that 22.3 percent of all adults online rely on the internet for health information. This study also found that 18 percent of the adult studied are inclined to purchase over the counter drugs online. Additionally, 23 percent of the adults studied purchase vitamins and supplements online. Other medical supplies online are purchased by 20 percent of the adults studied.

Similarly, a recent Healtheon Corp Internet survey of the field revealed that 85 percent of physicians are currently using the internet, a marked increase of regular online activity by physicians. This survey chronicled the computer needs and expectations of almost 10,000 physicians. The survey found that more than 63 percent of the physicians surveyed use email daily and that 33 percent have used email to communicate with patients.

Doctor-patient communication via email has jumped 200 percent in a recent twelve month period and nearly 20 percent in a recent three month period. Electronic communications between patients and doctors was statistically insignificant when physicians were first surveyed in 1997.

Many references teach the use of telecommunications to provide services. For example, U.S. Pat. No. 5,434,611 issued to Tamura (Tamura) on Jul. 18, 1995 teaches the use of a cable system for bidirectional audio/visual communication and transmission of data including data obtained from monitoring equipment. Alternately, a system taught in U.S. Pat. No. 5,441,047 issued to David et al. (David) on Aug. 15, 1995 can be provided with separate transmission of monitored physiological data over a telephone line rather than a cable system.

Another reference teaching remote monitoring of physiological parameters and transmission of physiological data to a medical care worker or expert system at a remote patient location during a remote consultation is U.S. Pat. No. 6,046,761 issued to Echerer on Apr. 4, 2000. Additional references teaching such transmissions include U.S. Pat. No. 6,731,324 issued to Levy on Apr. 4, 2000, U.S. Pat. No. 5,462,051 issued to Oka et. al. (Oka) on Oct. 31, 1995 and U.S. Pat. No. 6,804,656 issued to Rosenfeld et al. (Rosenfeld) on Oct. 12, 2004.

Additionally, access to a database, emergency services, a specialist, or ambulances during remote consultations is taught. See for example, David, U.S. Pat. No. 6,638,218 issued to Bulat on Oct. 28, 2003, U.S. Pat. No. 6,731,324 issued to Levy on May 4, 2004 and U.S. Pat. No. 5,619,991 issued to Sloane (Sloane) on Apr. 15, 1997. Furthermore, Rosenfeld teaches monitoring patient rooms from a remote location having access to a number of different databases for improving the care of the patients.

Additionally, Oka teaches a medical worker transmitting instructions in response to information received from the remote location in such a system. Bulat teaches transmitting a prescription to a pharmacy in response to a consultation in such a telecommunications system. A single channel is used for transmitting the monitored physiological data from the patient to the health care worker in Oka. Additionally, the use of multiple channels for transmitting the parameters is taught. For example, Bulat teaches providing a physician with an audio/visual link to a remote patient terminal by way of a telephone system, as well as links to patient, medication and protocol databases by way of a LAN.

The use of a remote consultation system to perform billing and payment transactions is also known. For example, Bulat teaches collecting credit card and insurance information in a remote consultation system. Echerer teaches providing an itemized bill, forwarding the bill to the patient by facsimile and accepting payment within the remote consultation system by means of a number of health management program cards.

U.S. Pat. No. 5,434,611 issued to Tamura on Jul. 18, 1995 is directed to a home health care system that uses a two way community antenna television network to permit remote communication between doctors and patients. Similarly, U.S. Pat. No. 5,619,991 issued to Sloane on Apr. 15, 1997 is directed to a system that facilitates the delivery of medical services using electronic data transmission. U.S. Pat. No. 5,748,907 issued to Crane on May 5, 1998 discloses an interactive real-time medical management system that can control many aspects of a medical practice.

Moreover, U.S. Pat. No. 5,987,510 issued to Imai, et. al. (Imai) on Nov. 11, 1999 is directed to a packet based telemedicine system for communicating video, voice and medical data between a central monitoring station and a patient monitoring station. The patient monitoring station obtains digital video, voice and medical measurement data from a patient and encapsulates the data in packets and sends the packets over a network to a central monitoring station. Since the information is encapsulated in packets in the Imai system, the information can be sent over multiple types of network architectures or combinations of network architectures. The video, voice and measurement data in the Imai system can be integrated and sent over a single network.

Similarly, David discloses an ambulatory patient health monitoring system for monitoring a remotely located healthcare patient from a central station. The David system includes instruments for measuring parameters of the medical condition of the patient such as heart rate, respiratory rate, pulse and blood pressure. The David system includes a first audio/visual camera disposed at the patient location and a second audio/visual camera disposed at the central station. The audio and video information obtained in this manner is transmitted between the patient's remote location and the central station via a communications network.

However, the David system is not network independent because the system data must be formatted in accordance with a different communications protocol for each of the different networks. Although the system disclosed in the David reference can send information between the healthcare worker and the patient via various types of networks, the information must be reformatted in different ways in order to be correctly used. Another disadvantage of the David system is that the audio and video data are sent over one communication network and the patient data is sent over another communication network.

U.S. Pat. No. 5,924,074 issued to Evans (Evans) on Jul. 13, 1999 discloses streaming compressed digital hypervideo received upon a digital communications network being. The compressed hyper-video is decoded and played in a client computer based video on a web VCR software system. Up to twenty-one past scenes can be displayed as thumbnail images within the system taught by Evans. Hyperlinks within the main video scene, and/or any of the thumbnail images, can be shown as hot spots, with text annotations typically appearing upon a cursor mouse over.

Thus, known systems such as the foregoing have provided valuable techniques for allowing service providers to bring resources to bear on providing their services to users at remote locations. However, they typically bring resources from only one or a few different sources to bear on the interaction at a time. Furthermore, the techniques for accessing the resources are cumbersome, and if the resources are accessed from different sources it is necessary to make multiple cumbersome accesses in order to obtain all of different resources. Such multiple accesses can involve getting through several firewalls and providing multiple sets of user identifications and passwords.

Specifically, there is a long felt need for technologies which facilitate the provision of information and services via a communication network. The telecommunication technologies can which can be facilitated can include real time interactive video or multimedia presentations. In particular, there is a long felt need teleconferencing for systems for providing such information via a plurality of platforms, including a wireless web, such that end users of the system can engage in an interactive exchange of information with service providers.

There is a particular need for systems which facilitate and supervise physician oversight and interaction with the patient. One of the recurring problems in providing health care, including remote health care, is that many patients fail to comply with recommendations made by their physicians. There is thus a long felt need for solutions which maintain closer interaction and monitoring between doctor and patient to permit monitoring of compliance. Additionally, it is important that such a system enable patients to maintain the confidentiality if their patient records. Furthermore, such a system should permit patients to have their risk assessments updated more frequently and provide real time one on one management.

All references cited herein are incorporated herein by reference in their entireties.

SUMMARY OF THE INVENTION

The system and method of the invention permits service providers to provide supervised teleconferencing, such as a supervised cyber office visit by a doctor or other health care provider, to a user located at a location remote from the location of the service provider, such as a home, an emergency room, a hospital or a nursing home. This permits the system and method of the invention to provide the advantages of advanced technologies, including large scale integration of the advanced technologies, to the remote locations. Furthermore, it permits multiple channels transmitting multiple applications to be displayed in predetermined location on a single graphical user interface. Accordingly, it permits sharing of data between the channels and supervision of web services.

A method for providing supervision to a teleconference including a service provider and a user includes providing a plurality of information channels for communicating information to the service provider and the user and integrating the information channels of the plurality of information channels to provide access to supervisory functionality for supervising the information channels of the plurality of information channels by way of a single portal. The method is adapted for providing access to audio/visual functionality by way of the single portal, providing access to information record functionality by way of the single portal and providing access to diagnostic functionality by way of the portal. Access to action functionality by way of the single portal and providing access to administrative functionality by way of the single portal are provided whereby the portal has access to the functionalities simultaneously. A single accessing of the portal by the user permits the user to gain access to all of the functionalities simultaneously in accordance with the single accessing. The portal can be a web portal. Each of the functionalities is access by way of a respective information channel of a plurality of information channels.

In another aspect of the invention a method for providing supervision to a teleconference including a service provider and a user includes providing a plurality of information channels for communicating information to the service provider and the user and integrating the information channels of the plurality of information channels to provide access to supervisory functionality for supervising the information channels of the plurality of information channels by way of a single portal. The supervisory functionality includes supervision of medical functionality and the record information functionality includes accessing medical records information. The diagnostic functionality includes monitoring at least one medical parameter to provide a monitored medical parameter. In a further aspect of the invention the supervisory functionality can include supervision of legal functionality.

In a further aspect to the invention a method for providing supervision to a teleconference including a service provider and a user includes a portal simultaneously having access to audio/visual functionality, information record functionality, diagnostic functionality, action functionality and administrative functionality. A single access of the portal by the user provides the user with access to all of the functionalities simultaneously in accordance with the single access. The single access is in accordance with a single sign in. The portal can be a web portal. Each of the functionalities is accessed by way of a respective information channel of a plurality of information channels.

In a further aspect of the invention a method for providing supervision to a teleconference including a service provider and a user includes providing access to audio/visual functionality by way of a portal, providing access to information record functionality by way of the web portal and providing access to diagnostic functionality by way of the portal. Access to action functionality is provided by way of the portal access to administrative functionality is provided by way of the portal wherein the portal has access to the functionalities simultaneously in order to provide supervision of the functionalities. With single accessing of the portal by the user whereby the user gains access to all of the functionalities simultaneously in accordance with the single accessing. The portal comprises a web portal.

A system for providing teleconferencing functionalities to a user includes a portal simultaneously having access to integrated audio/visual functionality, information record functionality, diagnostic functionality, action functionality and administrative functionality to provide supervision of a teleconference. A single access of the portal by the user permits the user to gain access to all of the functionalities simultaneously in accordance with the single access. The single access comprises a single access in accordance with a single password. The portal is a web portal.

A method for providing teleconferencing functionalities to a service provider and a user includes providing access to supervisory functionality by way of a portal and providing access to information record functionality by way of the web portal. Access to diagnostic functionality by way of the portal is provided and access to action functionality by way of the portal is provided. Access to administrative functionality by way of the portal is provided wherein the portal has access to the functionalities simultaneously.

The present invention is in one embodiment directed to a system for providing two way communication network access to information for such diverse areas as medical information, corporate information, law, government, entertainment, fitness, elder care, educational information and any other type of information. The invention utilizes and can incorporate a host of technologies including broad bandwidth, network resources, optimized routing, negotiated transport, two way voice-recognition, audio/visual real-time one on one supervision, data analysis and data intelligence, real time patient vital sign recording and clinical testing and on line examination. Compliance, prevention, evaluation, diagnosis, personalized content and clinical treatment can be facilitated in a secure on line Internet, Internet II or channeled delivery network using any type of telecommunications system. For example, fiber, satellite, television, cable and wireless technologies can be used.

The present invention provides an easy to use mechanism for users such as medical care providers and patients to obtain information, this permitting practitioners to provide one on one care. The invention can be utilized as part of a contracted, time based usage subscription service in which utilization of bandwidth and time can form the basis for revenue generation. The usage determination can be adjusted for medical coverage parameters.

An important feature of the invention is the provision of one on one real time audio visual interaction between a user and a health care provider or other person. The invention can permit providing and/or enabling and facilitating supervision including voice, image and remote online and wireless inquiry and examination. The invention can be used for instruction, education, training and communicating vital signs or other medical information. Knowledge tests can be facilitated within a proprietary secure integrated multichannel, multi portal network. Individualized users, providers and supervisors can be provided with customized and integrated connectivity, engineering, networking and software by way of a GUI. The GUI makes it easier to move data from one application to another. The GUI can have standard formats for representing text and graphs. Because the formats are well defined different programs can run under the common GUI and share data. Furthermore, the GUI can serve as a custom client for supervising the providing of any type of service. Such integration and supervision of communication between service providers and their clients permits seamless intelligent software controlled access to and from multiple high bandwidth delivery mechanisms and devices by way of a number of information channels.

The invention is designed to promote active participation of all individuals involved in providing the remote services. For example, all levels of the healthcare industry including patients, physicians, providers, insurance companies, managed care companies, rehabilitation and exercise facilities and government agencies involved in total patient well being can participate. In the medical context, for example, the present invention provides for the interactive exchange of patient data, vital signs and status in real time during the exchange.

The present invention can incorporate a core which has extends multi channel one on one remote supervision for many different industries. The supervision web services of the invention can access and supervise applications relating to any field of art. It can be advantageously applied to applications in telemedicine and collaborative healthcare for remote consultation and monitoring of patients. The invention can utilize the connectivity between high bandwidth providers to form a cyber superhighway that enables one on one audio/visual real time supervision and facilitates connectivity for channeling content into a unified platform that is customized for specific target multi-industry applications. The invention can utilize integrated connectivity to make any content available by way of a single access to a single e-commerce portal. This important feature of the invention is provided by means of a centralized plug in capability. This capability enables users to mold and standardize information technology and e-commerce providers into a verified interaction in a simultaneous one on one real time supervision environment with a single portal for access to all of the resources.

Thus, the invention can enable a cyber superhighway based a single portal to function as a backbone template. This enables high bandwidth technology companies, information technology companies, and any other type of commerce companies to maximize their valuation. In effect, the invention can be a facilitator and supervisor to enable companies to utilize audio/visual one to one real time supervision on the internet or private network with their client's and customers.

As previously described, the present invention can be very advantageously applied to the health care industry. The present invention provides core functionality including supervision comprising live one to one audio/video supervision. The invention further provides records and a history associated with interaction between service providers and users. In the case of medical supervision applications, electronic medical records (EMRs) showing information such as charts, doctors' notes, pre-stored audio/video streams, etc. can be provided to the users.

The invention can include a diagnostic alerting system along in response to monitoring using medical instrumentation. The invention can permit testing of a patient to be performed in real time during the interaction. An action may be interfaced with partnering companies. In the case of medical supervision channels may be labeled as e-health and treatment channels, thereby bringing audio/video capability between doctors and pharmacists for products, sales and other services. The other services can include, but are not limited to, dietitians, therapists etc. Administrative functions, such as billing, auditing and accounting can be performed while the supervisory sessions are in progress thereby increasing efficiency and decreasing errors. For example, simultaneously users can interface with insurers who can interface with service providers.

It is to be noted that the invention provides for multiple channel supervision environments. In one embodiment multiple different information streams including audio/video or virtual electronic records channels can be simultaneously available to the physician and patients during supervision procedures. A high speed channel within the system can provide supervision and contain the audio/video streams necessary for the live one on one supervision activities such as those involved in telemedicine applications.

A second channel can provide records and can contain personal information of the user in the form of electronic medical records, EMRs, etc. The information can include charts, doctors' notes, selected portions of audio/video sessions, etc. A third channel can provide diagnostics and refer to specific real time alert signals generated from tests run simultaneously on medical instrumentation results. The signals from the medical instruments can be compared to records information and audio/visual streams stored in many other locations. A fourth channel can provide e-health or e-treatment capability to the system and automatically generate orders such as prescriptions. The orders can be supervised by the doctor who can review them and add an electronic signature. The fourth channel can also interface with locations such as pharmacies and allow patients access to information about their treatments stored in many other locations.

A fifth channel can provide administrative and other management functions needed for each interaction. For example, user billing, insurance filing and purchasing of required supplies can be permitted. Another possible feature of the administrative channel can be matching inventories to the user's needs possible orders can be automatically generated when necessary due to materials being out of supply. Interfaces with hospital administrative systems can be transparent to the user. It is to be noted that the administrative channel scenario can involve any other services in addition to prescribing.

A Palm-like or other hand-held device may support a cellular phone or WLAN connections to the system and the user. In one example, a doctor may write a prescription. The system can automatically send the prescription for pre-authorization to the insurance company. The patient can pay the normal co-payment to the insurance company or the physician during the telecommunication session. The Palm like device or other hand held device may be used by the doctor's staff to update the patient's electronic medical records in real time. The structure of the invention allows for partnering technologies, as well as links to insurance companies. This permits electronic filing of claims and faster insurance reimbursement to the physician or patient.

BRIEF DESCRIPTION OF SEVERAL VIEWS OF THE DRAWINGS

The invention will be described in conjunction with the following drawings in which like reference numerals designate like elements and wherein:

FIG. 9 shows typical information that can be integrated when the present invention is applied to the medical field;

FIGS. 10A, 10B show block diagram representations of graphical user interface and a central server which can be used with the system of the present invention;

FIG. 14 shows a block diagram representation of a certificate authority which may be used with the system of the present invention.

DETAILED DESCRIPTION OF THE INVENTION

The present invention is specifically directed to a system for providing online, interactive content and audio/video presentations and systems between a service provider and a remote user of the service. In one embodiment the end users may be doctors and patients. In other embodiments the end users can be an attorney-client, real estate broker-customer or any other pair of commercial users who need to provide content and information to each other. Thus, while the present invention is sometimes described in the context of the provision of medical information and care for illustrative purposes, it is to be appreciated that the present invention is applicable to a wide array of markets and applications.

Figure 1:
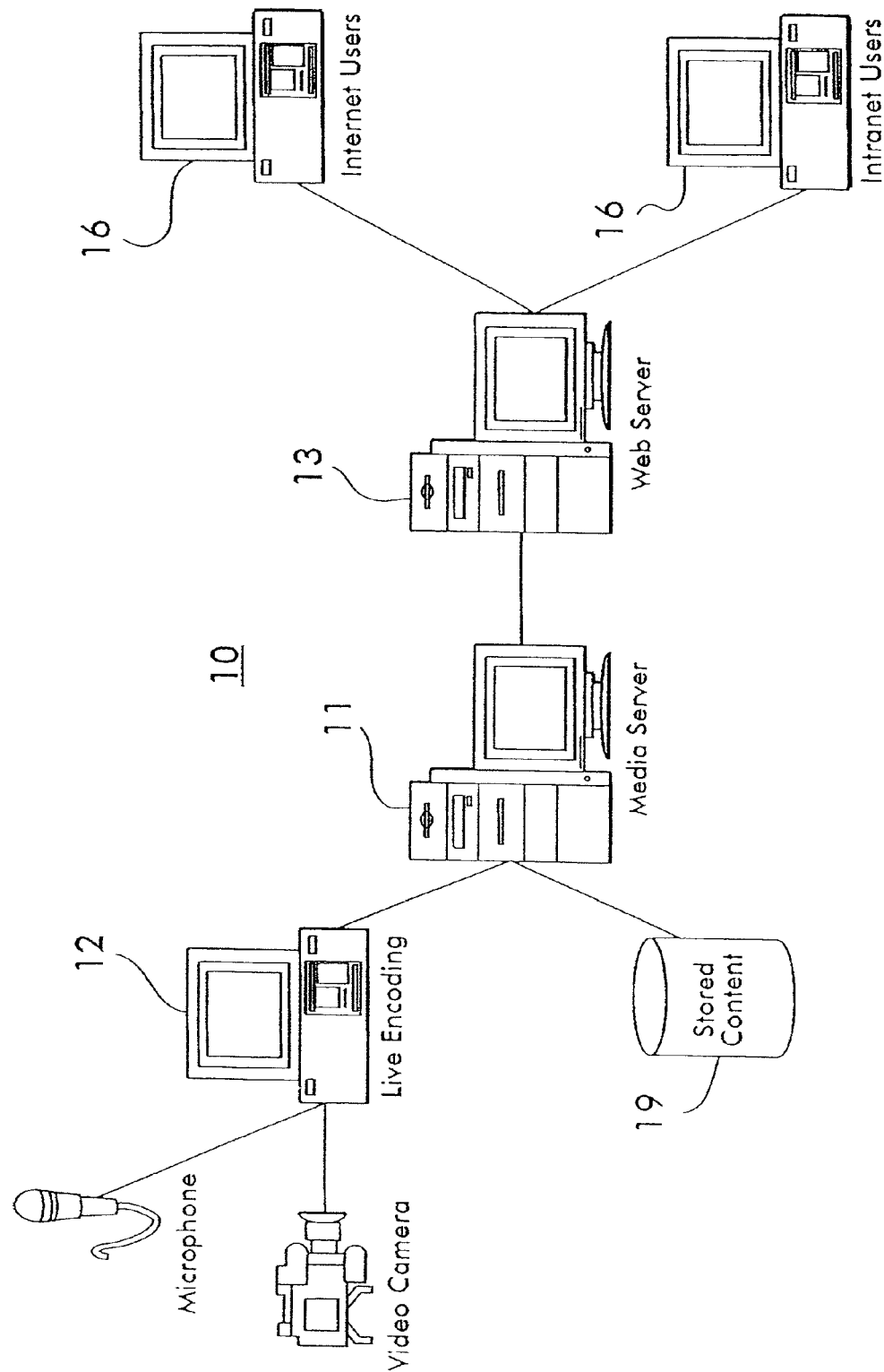
FIG. 1 shows a block diagram of a media broadcast suitable for use with the present invention.

Referring to FIG. 1, there is shown a proposed diagram of the system 10 of the present invention. In this embodiment, the present invention can be a dynamic content driven web application. However, it will be understood by those skilled in the art that any type of communication network can be used in keeping with the scope of the invention. The preferred embodiment can include an internet web application that provides a plurality of content including searchable information, FAQs, articles and chat rooms. The preferred embodiment of the invention also has the ability to engage in one on one real time sessions between a service provider and a user such as a medical patient or a legal client by way of the computer 16, for example, using the known HTTP or MMS protocols.

When the system is applied to the field of telemedicine the patient may be bed ridden or in a nursing home or any other location accessible via a computer or TV module. The invention can incorporate voice recognition technology to permit both physicians and patients to input data into the system. An important feature of the present invention is the provision of online monitoring and examination between the service providers and the users. Specifically, the present invention provides for and facilitates one on one real time supervision between the service providers and the end users. The content provided can be searchable by key word or phrase. This allows end users to quickly locate information within the system 10, which relates to a specific area of interest or need the end user may have. By utilizing a database driven system, a user of the invention is able to quickly locate information on a desired basis.

The present invention has a number of uses and applications, including the ability to push updated information to users to send email notices, to enable users to continue to use the programs available from the site when offline to provide content and audio video formats to enable end users to track their own progress when using programs, to receive dynamic risk assessments and to locate health/care services and providers.

As shown, the system 10 can include two dedicated servers 11, 13, for example, a web server, a Microsoft Media server such as a Windows 2000 server or a Real Media Server. The servers 11, 13 can run in a single computer. The system 10 further incorporates video processing software such as video conference software applications and databases integrated with streaming video systems based on solutions of the kind of the Real Networks Digital Media Solutions products family. Thus, the system 10 could support Universal Media Delivery, Modular architectures, standards-based solutions supporting RTSP, SMIL, XMCL, MPEG and major operating systems. The system 10 can be able to deliver rich media via Internet-enabled devices. The system 10 also can incorporate large data storage 19 and security for sensitive information and the information that may need to be accessed by various types of users. The server can communicate with a live encoding personal computer 12, for example, using HTTP or MS BD protocol.

The present invention can be directed to a comprehensive system for facilitating the provision of medical and health related information, including real time audio video one-on-one interaction between an end user and a server provider. Furthermore, it is to be appreciated that the present invention is applicable to any field of endeavor where information is shared among end users. Non-exclusive examples include the legal, financial services, banking, accounting and engineering fields. It is to be appreciated that the teachings of the present invention are thus applicable to other fields of use and areas in which information need to be shared and conveyed by and among end users. The present invention can provide selectable audio/visual channels, diagnostic information and data, news, clinical information in a wide array of medical areas, training, education and eldercare, wherein it is possible for any of the channels to transmit audio/visual information if desired. Furthermore, the audio/visual information may be applied to the channels in any manner known to those skilled in the art.

In a preferred embodiment set forth herein for illustrative purposes the invention can be practiced using five communication channels or information streams. However, it will be understood by those skilled in the art that the number of channels or information streams used is not critical, as long as they are integrated and supervised to provide a portal for permitting a provider of services to provide the services to a user at a location remote from the provider as set forth herein below. The integration of the channels permits the functionality to access structured and unstructured information and make it available for analysis, editing and display.

The five channels used in the illustrative embodiment herein can be: 1) a supervision channel including the audio/visual streams to permit live interactive supervision activities, for example, between the provider of the services and the user, 2) a records channel including access to personal information of the user or other information relevant to providing the services, 3) a diagnostics channel including information according to devices such as real time sensors or monitoring equipment to provide alerts or permit other responses to the information available from the integrated channels, 4) an action channel to permit the provider of the services to take actions based on the information available from the integrated channels and 5) an administrative channel for providing management functions required in order to provide the services to the user. All five channels are integrated and synchronized and can contribute to providing the supervision of the teleconference in accordance with the inventive system and method.

When the present invention is applied to the field of telemedicine the supervision channel can permit live interaction between a health care worker, for example a doctor and a patient. In such an application, the records channel can permit access to sources such as electronic medical records and EMRs including information such as charts, doctors' notes, portions of previous audio/visual sessions, etc. The diagnostics channel can be used to transmit real time alert signals generated from tests run on medical instrumentation results. The action channel can generate, for example, a prescription for a doctor's review and an electronic signature and can have direct access to facilities such as pharmacies.

An example of a supervision application suitable for integrating and supervising the foregoing channels is also set for herein below. However, it will be understood that any number of differing applications can be provided by those skilled in the art to provide the integration and supervision of the channels required to provide the services to a user at a remote location according the invention.

Figure 2:
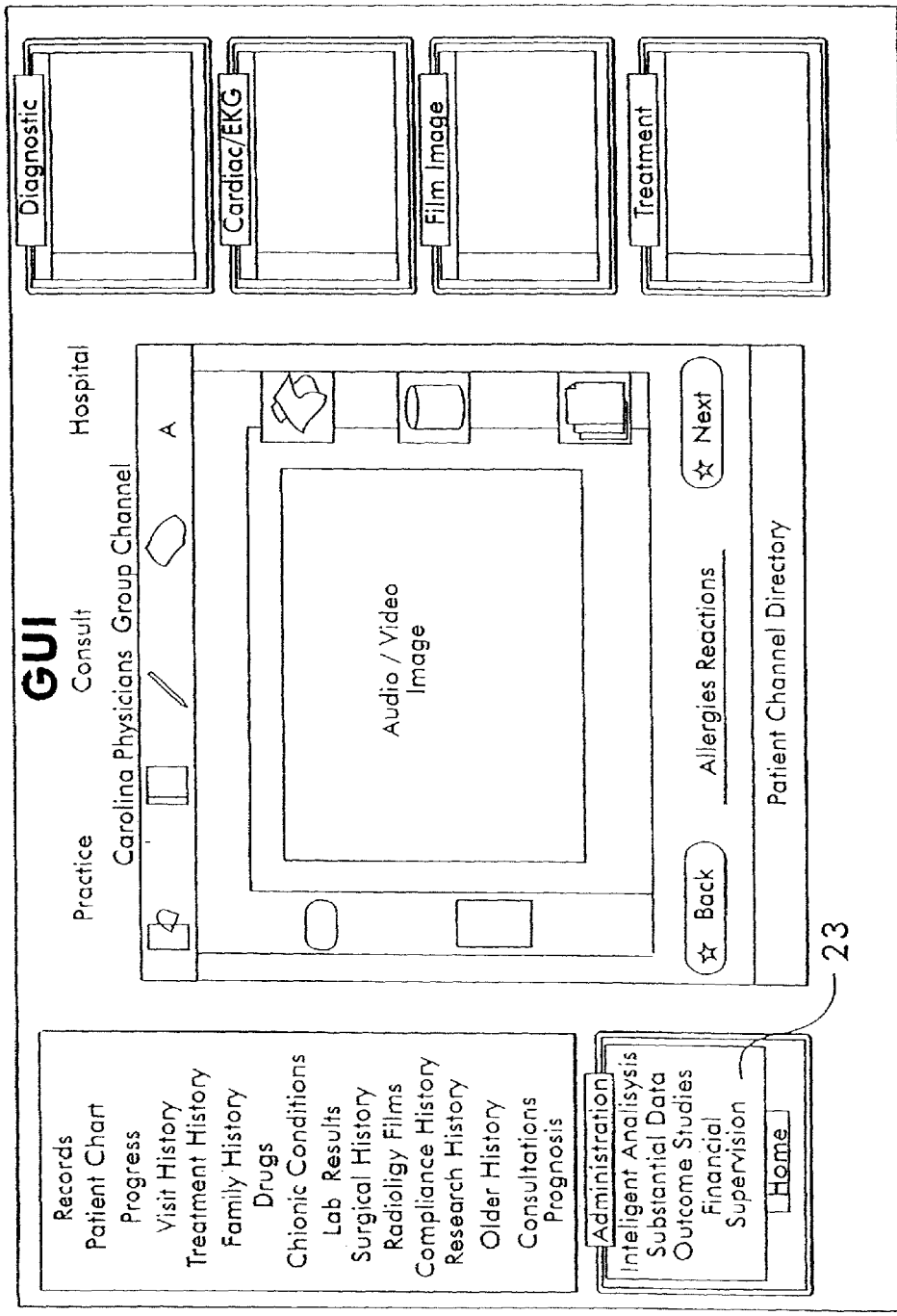
FIG. 2 shows a screenshot of a graphical user interface display block diagram of a prospective end user system in accordance in the present invention that may be presented in accordance with the present invention.

Referring now to FIG. 2, a video display interface display 25 of a comprehensive interactive system in accordance with the present invention is shown. The video display interface display or GUI 25 can be used to display, for example, records of consultations, hospital records, diagnostics, EKGs and film images when the invention is applied to the medical arts. The patient's treatment regimen including pharmacology, products, services, programs and information can also be displayed. The display interface of the system 10 can incorporate an administration module 23 which can provide intelligent analysis, statistical data, outcome studies, financial data and supervision. During real time one on one communication and interaction the system 10 can record information such as patient history, prognosis, visit history, treatment history, family history, drugs, chronic conditions, lab results, surgical history, radiology films, compliance history, research records, oral history, consultations and prognosis, for example, using the server 13.

Figure 6:
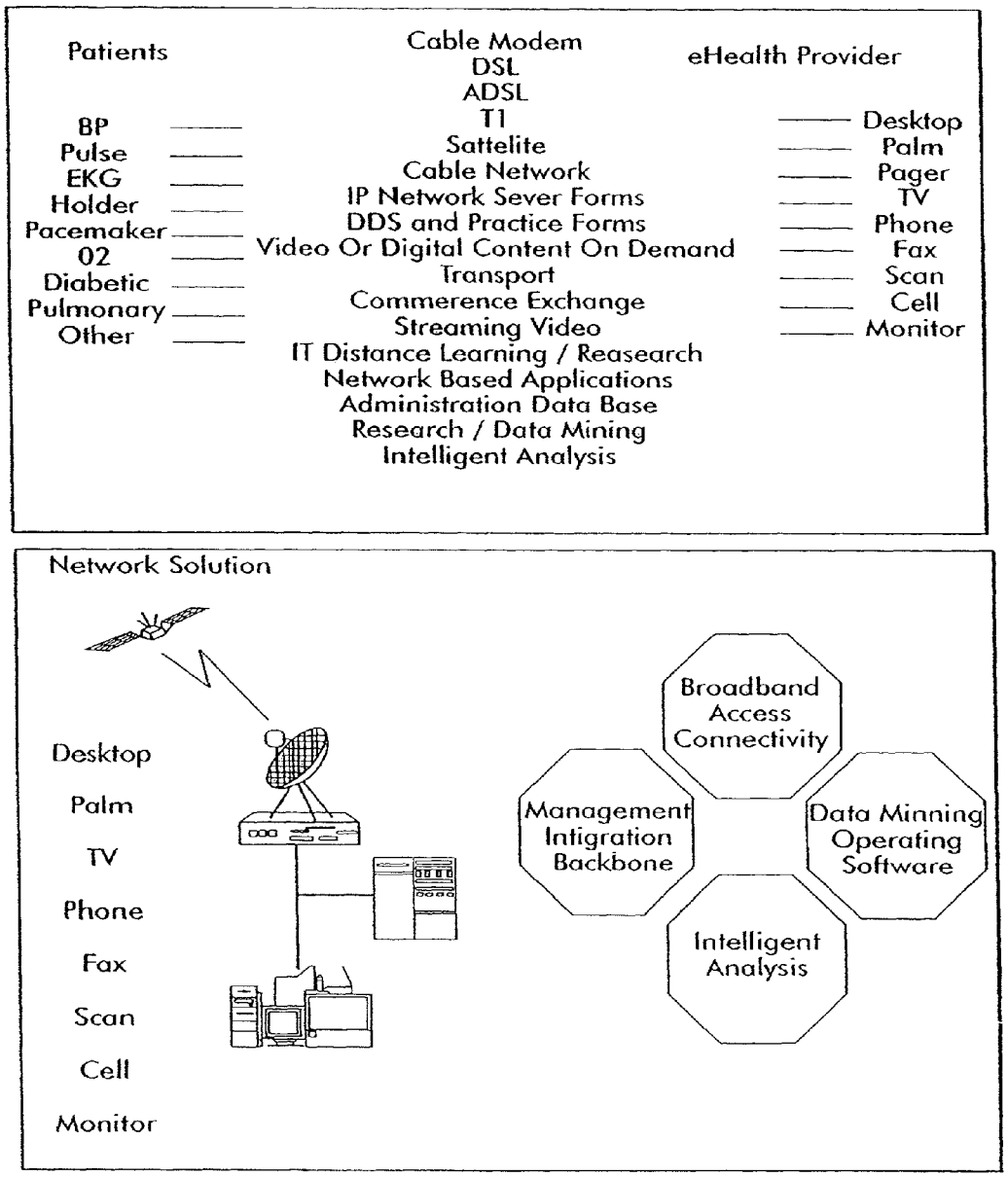
FIG. 6 shows a graphical representation of a network backbone in accordance with the present invention.

The central image of the interface display 25 can be accessed by the physician to obtain information about the patient such as allergies and reactions. The system 10 thus creates one on one real time audio visual interaction between the end user and the provider and enables and facilitates supervision including voice, image and remote online & wireless inquiry, examination, instruction, education, training, vital signs and other medical information, knowledge tests and markers within a secure integrated multi-channel, multi-portal network such as shown in FIG. 6. The network can be individualized to patient, individual, provider and supervisor with customized and integrated connectivity design, engineering, networking, and software to provide seamless intelligent software controlled access to and from multiple high bandwidth delivery mechanisms and devices.

The invention facilitates centralized access to individuals, one on one, in an interactive visual and voice online, satellite, wireless integrated secure environment for the purpose of providing supervision in real time. This capability permits on line examination with concurrent access to records, charts, test results, history, tests, research, data, billing mechanisms, data marts, medical images, correspondence, notes, files, vital signs, real time diagnostic testing results, images, consultation, pharmacology selection, detailing, alerts, transcription, conferencing, outcome data and research, reference and treatment options within a single screen/portal/channel. In a broader sense as shown in FIG. 6, the present invention thus provides a comprehensive system including broadband access and connectivity, data mining and operating software, and a fully integrated backbone.

Figure 3:
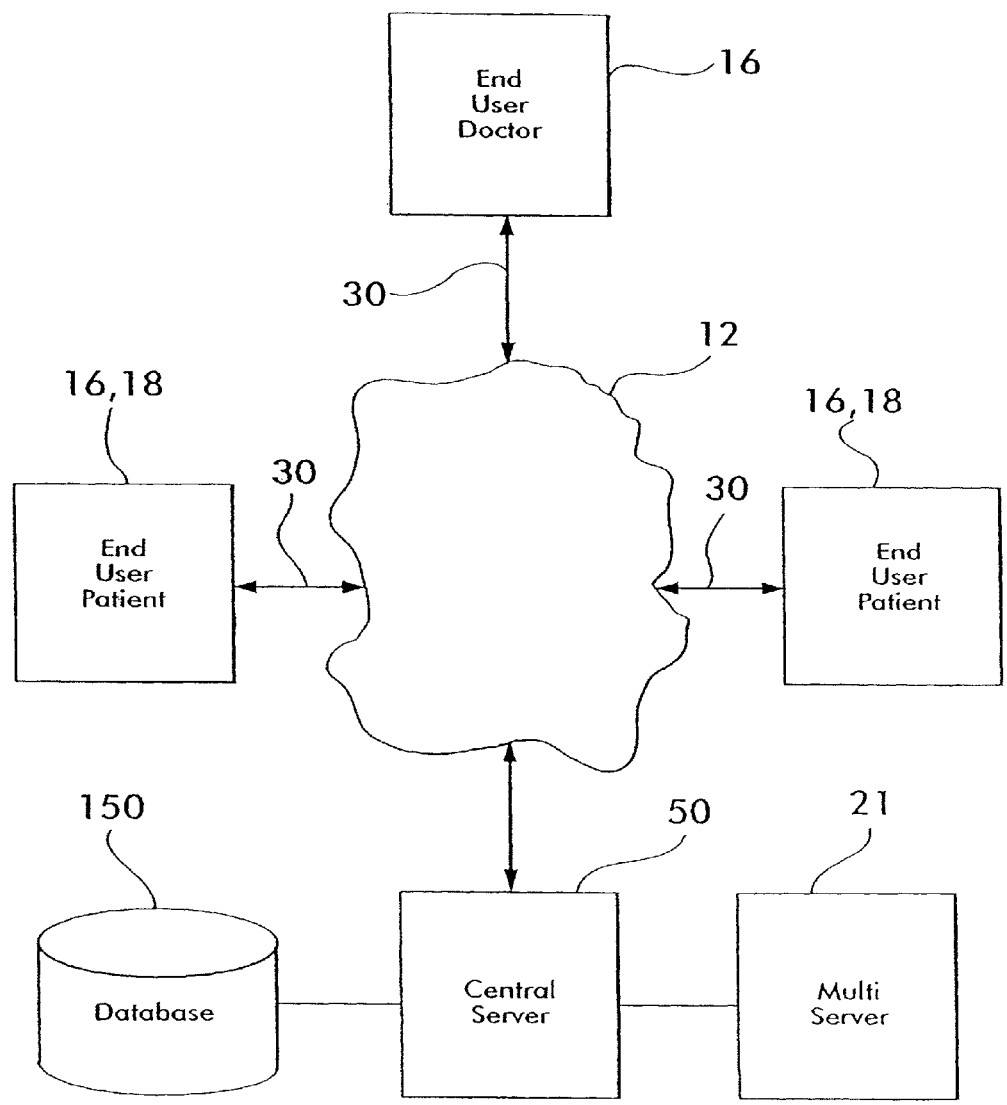
FIG. 3 shows block diagrams of a system in accordance with the present invention.

Referring to FIG. 3, there is shown a block diagram representation of a preferred embodiment of the present invention. From a structural and operational standpoint, a preferred embodiment of the invention comprises a central computer server 50 connected by a computer network 12 such as the internet to remote end user stations 16. The central server 50 connects to a database 40. In a preferred embodiment, the end user stations 16 can comprise a plurality of healthcare providers and patients linked to the computer network 12 via a transport medium 30. Preferably the central server 50 provides a website such as www.uspreventivemed.com which can host a set of content and tools for health and medical applications of the invention. The website can provide a host of database driven content related to health and wellness including multimedia presentations, FAQ, articles, chatrooms and bulletin boards. A critical feature of the invention is the provision of audio-visual interaction between the end users 16 as well as diagnostic interaction. Thus, home monitoring of patients during a cyber office visit is possible.

The end user 16 as noted above, in a one preferred embodiment, can be linked via a global computer network 12 such as the Internet, intranet or worldwide web. However, but other embodiments including LANs, WANs, many different types of intranets or any other type of communications system can fulfill the spirit and scope of the present invention. End user system 16 can be any devices that interconnect to the system via a network or other IP transport methods. They include, but are not limited to, such devices as televisions, computers, hand-held devices, cellular phones, land based telephones, wireless electronic devices and any device which can use a transport medium such as the transport medium 30.

Non-limiting examples of a transport medium 30 applicable for use in the present invention can include any backbone or link such as an ATM link, FDDI link, satellite link, cable, cellular, twisted pair, fiber optic, broadcast wireless network, the internet, the worldwide web, local area network (LAN), wide area network (WAN) or any other kind of intranet environment including a standard Ethernet link. In such alternative cases, the clients can communicate with the system using protocols appropriate to the network to which the client is attached.

The present invention may comprise a multi server 21 environment which comprises a computer system in accordance with the present invention that allows the multiple users 16 to communicate with the system. Through communication links such as the transport medium 30 the end users 16 can be linked to a server such as the central server 50 preferably by a customizable interface to be described in greater detail below.

Figure 4:
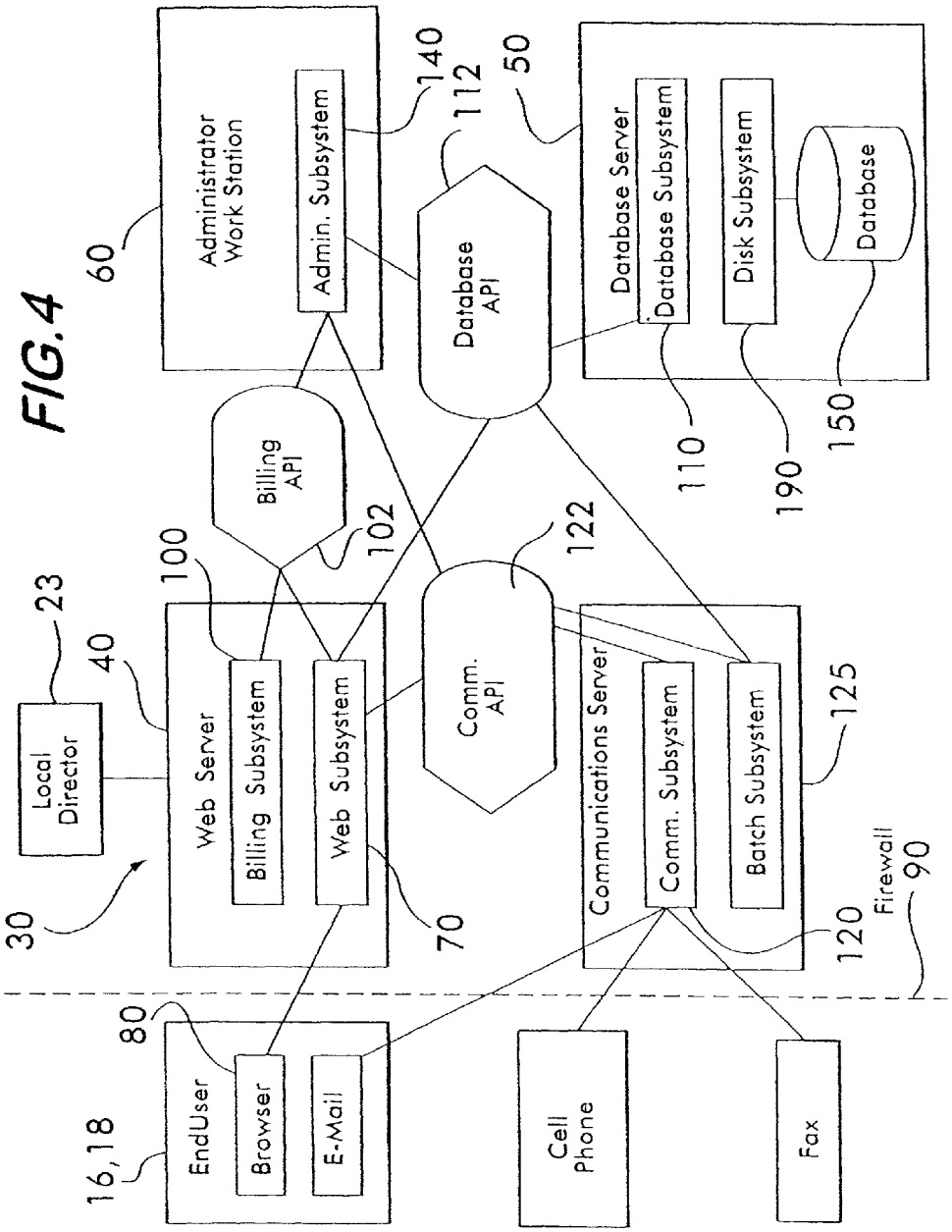
FIGS. 4, 5 show a more detailed representation of the central server and database systems of the present invention.
Figure 5:
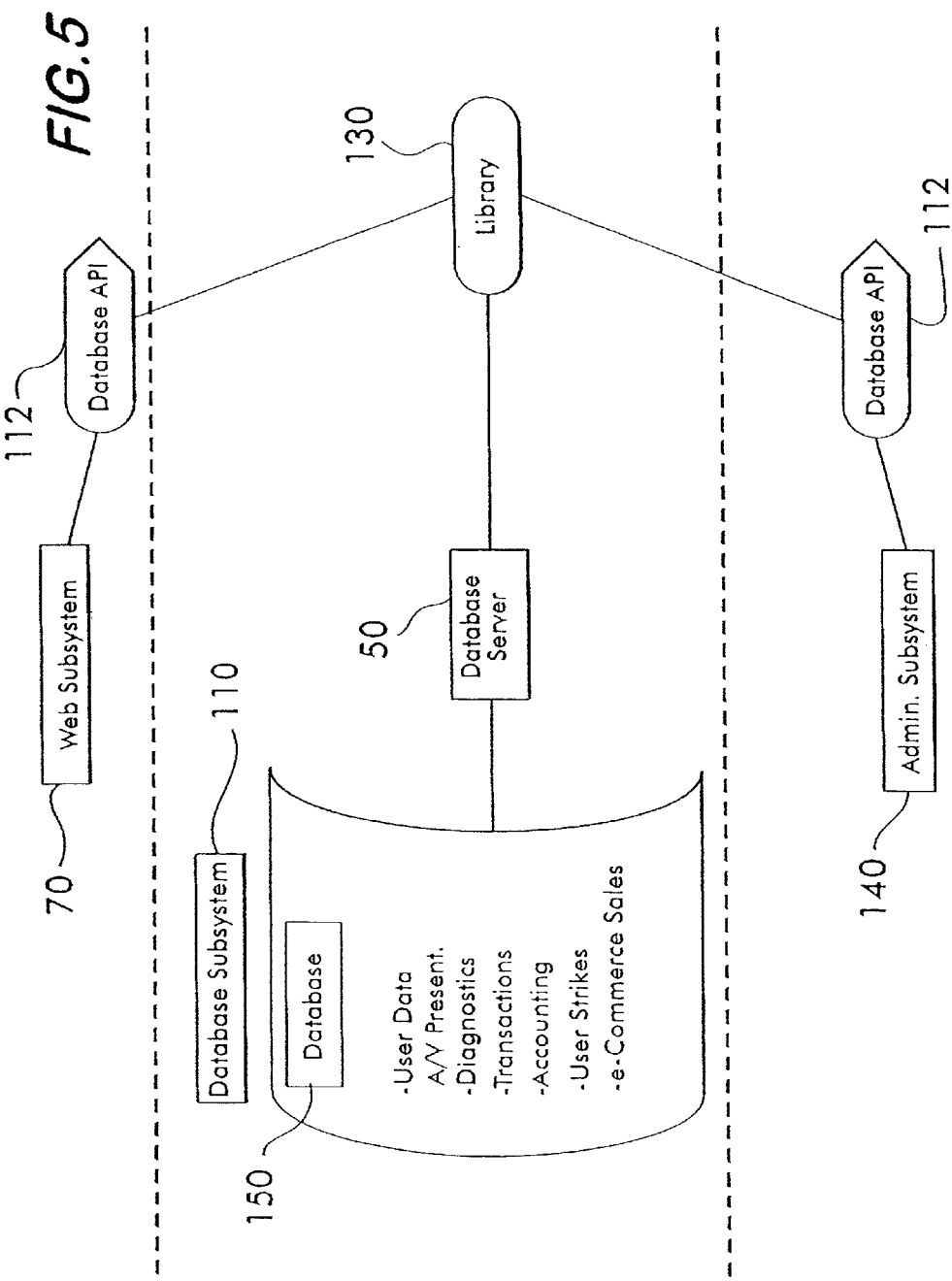

Referring to FIGS. 4 and 5, the central server and database systems of the present invention are shown and described in greater detail. A local director 23 as shown in FIG. 4 routes signals through the system to the various servers, to be described in more detail below, and to and through the transport medium 30 to the browsers 80 of the end user 16. All routing of information can be performed over virtual paths. The system preferably includes two primary servers, a web server 40 and a database server 50 which may operate using such database platforms as SQL server or Oracle. Hence, in one embodiment the SQL server may run SQL server database management software from Microsoft Corporation. Alternatively, the server can run an Oracle database server. As noted above, the system can also incorporate media servers.

The system further includes an administrative workstation 60 as shown in FIG. 4 or system which can provide the administrative capabilities and monitoring for the system under the control of an administrative subsystem 140 within the administrative work station 60. The administrative workstation 60 allows administrators or other operators to filter information and perform routine operations which affect the entire system. Such operations can include, but are not limited to, administering the accounts of, for example, healthcare providers and patients, ordering and control of products to be sold through the website, back end functions, adding or deleting new users, tabulation of printing reports and performing backups and maintaining the programs within the overall system.

A web subsystem 70 as shown in both FIGS. 4, 5 can be responsible for interactions with a web browser 80 at the locations of the end user devices 16. The web subsystem serves as an end user interface to the system. Interactions between the devices 16 and the database subsystem occur through the web subsystem 70. An Internet Information Server (IIS) 200 by Microsoft Corporation is an exemplary web server which can be used as the subsystem 70 in accordance with the present invention, although the present invention is in no way limited to this system. The expression of the user interface presented to users 16 in their client devices may be implemented as HTML or any other high level computer language or technology known to those skilled in the art, and may be displayed in a standard web browser 80 including a wireless browser 80.

All systems described herein can communicate by way of a gigabit Ethernet Base T network and a switching hub. The web server 40 can send HTML or other high level computer language to the end user work stations 16, validate passwords, send logging and transaction information to the database server 50 and perform logical operations, thus behaving as a transactional server.

In one embodiment, the server operating system may be a Windows NT server, a multi-platform operating system provided by Microsoft Corporation and can include media servers. The Sun Microsystems Solaris is one alternative embodiment. The server typically includes IIS, which is a completely integrated internet application platform. IIS includes a high-performance web server, an application development environment, integrated full-text searching, multi-media streaming and site management tools. The security infrastructure is integrated within the server, thus enabling an easy-to-maintain and highly secure web development and deployment environment.

The operators of the system may create, delete and update account information utilizing the administrative subsystem 140 (as shown in FIGS. 4, 5) in the administrator work station 60. A billing subsystem 100 (as shown in FIG. 4) can be responsible for credit card, debit card or checking account verification and any other necessary billing type functions. Database subsystem 110, communication subsystem 120 and billing subsystem 100 can thus execute essential services for other parts of the system, and can therefore have well-defined application program interfaces (API) 112, 1122, 1102, as is well recognized by those with skill in the art. The system will preferably be protected for the internet by a firewall 90 which is a safety precaution, and important with respect to the present invention due to the sensitive and confidential nature of some of the material in the databases.

In a preferred embodiment, databases such as the database subsystem 110 store pertinent information pertaining to end users 16 transactions and account history, as well as general dynamic system information. All interactions with the database subsystem are performed through a database API 10 which may define the interface to a library 130 of stored procedures as shown in FIG. 5. These are used to implement high-level database functions and to shield the details of the database implementation from the other subsystems. The database subsystem 110 is preferably implemented using the database server 50. The databases contain such information as user information, records, account status, the inventory of items available for sale, content, multimedia presentations and medical histories.

The administration subsystem 140 as shown in FIG. 4 provides an interface for operators and managers of the system to modify the database, print reports, view system data and log user information. The administration subsystem 140 provides a collection of access forms, queries, reports and modules to implement the administration interface. Administrators can typically have the power within the system to force most actions. The administration subsystem 140 will interact with the communications, database and billing subsystems.

The communications subsystem 120 is interfaced to a communications API 122, for example, to notify the end users 16. Users 16 may be notified by telephone, fax, email or pager, or other communications devices, which can be contacted by the system 125 as shown in FIG. 4. Some portable telephones and pagers can include email addresses and so may be contacted by the email system. Other users may have only telephone numbers. Other interfaces may be utilized as the application so demands.

A batch subsystem 125 within the communications server of FIG. 4 may periodically send out grouped notifications. It will access the database subsystem 110 to determine what notifications are required, and use the communication subsystem 120 to make the notifications. The billing subsystem 100 may be used to verify and bill credit cards, where applicable, and communicate through the billing API 102 with the administration subsystem 140. Furthermore, the billing subsystem can potentially communicate with an outside billing and verification service which could be used to perform the billing functions.

Referring to FIG. 5, the database server 50 which can implement the database subsystem 110 of the present invention comprises a server that can maintain all associated logging and transaction information for the system. Through the database 40 (which can be backed up by a backup database for safety purposes), the database server 50 logs user setup, account creation information, diagnostic information and tests, maintains and tabulates transactions and collections. It also hosts backup operations and performs statistical calculations for the entire system.

The database server 50 is preferably a dual processor computer microprocessor. Each connection to the database 150 and its associated information may be handled by a separate thread within the database server 50 processor space. It is anticipated that a dual processor machine may be sufficient for the type and amount of transactions that it will be performed. However, if a dual processor proves insufficient, the database storage can be implemented in two or more machines to distribute the server load.

The disk subsystem 190 shown in FIG. 4 of the database server 50 may comprise a vulnerable and crucial server element. Due to the critical design of the subsystem, it is preferable to utilize a device such as a Level 5 RAID. RAID is an alternative to standard SCSI hard disk drives. A RAID system provides automatic recovery from hard drive failures. Level 5 RAID systems provide the best balance between cost and level of data protection. A system such as the Level 5 RAID system can use multiple hard disk drives on which the stored data can be recorded redundantly using a scheme by which the data on the disk can be completely reconstructed in the event that one of the disk drive units in the RAID fails.

In the event of failure, the failed drive can be removed from the RAID system while it is still operating and a replacement drive can be installed. A system such as the RAID system can regenerate the data and return itself to full protection capability. The data sorted on the disk subsystem remains available for normal processing, that is, from the time the drive fails to the time the RAID system is returned to full protection capability. Other levels of RAID which are less costly do not offer this type of data availability and could translate into costly system downtime.

In one embodiment, there can be one operator workstation 60 used for administering the system. As the need for additional workstations arises, additional operator workstations can be added by adding additional computer systems, installing the administration software and connecting them to the LAN. Operator workstation machines preferably utilize a Windows operating environment manufactured by Microsoft Corporation.

In view of the above operational environment, the present invention is now described in the context of a web-based system for providing online, interactive content between any number of end users 16. In one embodiment, the end users 16 can include a doctor and patient. In other embodiments, the end users can comprise an attorney-client, real estate broker-customer, or any other pair of commercial users who need to provide content and information to each other.

By utilizing the system of the invention the end users 16 are able to quickly locate information on a desired basis. The present invention has a number of uses and applications, including the ability to push updated information to end users to send email notices and to enable users to continue to use the available programs when offline. This permits providing content and audio video formats enabling end users 16 to track their own progress when using program receiving dynamic risk assessments and locating health-care services and providers. The system incorporates data storage and security for any type of sensitive information.

Many other applications are made available by the present invention. Both federal and state prisoners are required to have medical and psychiatric care. This could be provided by the present invention. Similarly the care of military veterans could be undertaken with the present invention, thereby realizing significant cost savings from information. The present invention could be used in the areas of rural or remote psychoanalysis. Some emergency services could also be provided in a one on one supervision environment in advance of transport or facility treatment. Post surgical monitoring in modern nursing homes is another medical application. Emergencies in nursing homes, monitoring and medical care could be provided by the present invention. As shown in FIG. 6, the present invention can provides a comprehensive system including one on one real time audio visual supervision, broadband access and connectivity, data mining, operating software and a fully integrated management backbone. The invention can thus provide service providers and end users full time supervision through audio/video contact for children, elderly or sick people where the audio/video can provide a direct diagnostics tool drastically enhancing intelligence gathering during supervision.

Figure 7:
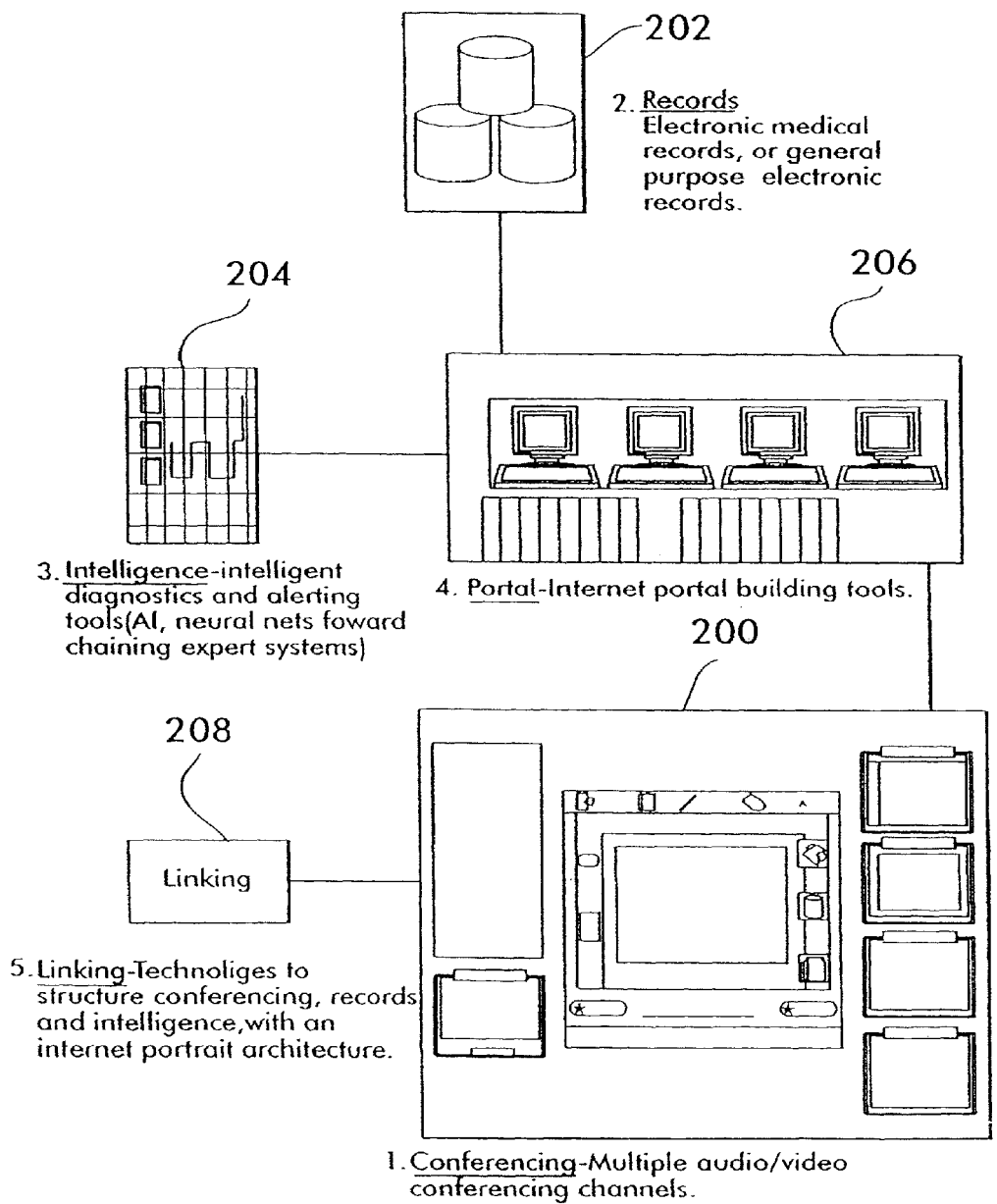
FIG. 7 shows a schematic representation of an alternate embodiment in accordance with the present invention.

As shown in FIG. 7, the supervision portal and data center of the invention provides for multiple channel supervision environments using linked channels. In one embodiment, five different information channels, or information streams (for example, audio/video or virtual electronic records channels) are simultaneously available to the service provider during supervision procedures. The channels can be distinct and can be located at different nodes. Furthermore, the supervised integration and synchronizing of the channels permits single portal access to all the resources made available to the system. The invention provides for selectability of audio video channels 200, in response to patient, user or institutional addresses which access records concurrently. The charts can be charts, history, etc. A faster channel can provide supervision and contain the audio/video streams necessary for live one on one supervision activities, such as those involved in telemedicine applications or other complex applications.

The second channel 202 can provide records and contain personal information of the patient (electronic medical records, EMRs) such as charts, doctors' notes, portion of audio/video sessions, etc. A third channel 204 can provide diagnostics and refer to specific real-time alert signals generated from tests run on medical instrumentation results which can be compared to records information and audio/visual streams. A fourth channel 206 can provide E-health or treatment services, and automatically generate prescriptions and present them to a service provider for review and addition of a electronic signature. It can also interface with pharmacies and allow patients access to information about their treatments via a portal.

A fifth channel 208 can provide the administrative and other management functions or linking functions needed for each application. The functions can include patient billing and insurance filing and purchasing. Purchasing can be another feature of the administrative channel where inventories are matched to patients needs and orders are automatically generated when necessary. Interfaces with hospital administrative systems can be transparent to the user in a preferred embodiment of the invention. FIG. 9 shows some of the information that can typically be transmitted within the system of the invention when it is applied to telemedicine. It will be understood that in an alternate embodiment channels two through five can also be provided with audio/visual capability if desired.

The administrative channel 20 can also include prescription services. A Palm-like or other handheld device may support a cellular phone and WLAN connections to the system and the patient. In an example, a doctor may write a prescription. The system could automatically send the prescription for pre-authorization to an insurance company simultaneously. The patient can pay the normal co-payment to the insurance company. The handheld device may be used by the doctor's staff to update the patient's electronic medical records in real time.

Thus, the invention can provide structured intelligence gathering from unstructured multichannel audio/video streams. The invention can be characterized by a number of features including multiple audio/video conferencing channels electronic medical records or general purpose-electronic records, the use of intelligent diagnostics and alerting tools and the incorporation of a portal which links tools and embeds technologies.

The invention can provide the means to interpret audio/video information thus opening up an unlimited number of applications. The invention builds intelligence from basic and massive information gathering and allows constant audio/video transmission and the simultaneous operation of store forward and real time audio/video in a single channel. The invention can also provide the progressive resolution control for selected elements in the audio/video stream within limited bandwidth systems.

The invention can provide for the full time supervision of children, the elderly, those requiring medical treatment and monitoring for security, medical and insurance purposes, etc. The invention incorporates medical instrumentation, survey and sensing equipment and measurement instrumentation of different types. The instrumentation can be supplemented with audio/video readings. It provides for 3-D visualization or wear-on pieces (bracelets, rings, helmet) for audio/visual supervision of patients. Voice to text translation and voice commands for the creation of time marks in the continuous supervision audio/video stream are provided in a preferred embodiment.

The system can monitor the ingestion of solids or liquids by an end user patient for internal physiological measurements. It can facilitate the reading of measuring instruments attached to the body of the supervised individual (be it living organisms, a machine, or a non-living entity). It further facilitates temperature and infrared visual and tomography measurements.

Another feature of the invention is the incorporation of multi channel intelligence and diagnostics with an intelligence engine, neural net matching and forward chaining expert systems. In this way the invention is applicable to or can link to multiple industries using equipment found in any corporation. Furthermore, the applications which can be advantageously used with the invention include treatment programs, guidelines, notes, orders, protocols, images, diagnostic data, consult sources, research information, outcomes, pharmacology data inserts, contraindications, clinical history, studies, papers, news, clinical data in geriatric, chronic, fitness, wellness, radiology, cardiology, psychology, human resource interview, training, educational, prisons, hospitals, clinics, treatment centers, elder care facilities, nursing facilities, rural tele-health, teleconferencing, live examination of patients, assessment, diagnosis and various treatment program applications.

The above can translate to the following three-stage functionality: (1) information, that is the pervasiveness of information, through multichannel availability and gradual implementation of technologies capable of extracting and structuring information from multiple non-structured audio/video data streams, (2) analysis of data and information by the healthcare professional and (3) response, through hyper annotation and linking between audio/video data and structured database records information and through real time response through diagnosis and alerting features. Other business implementations may follow architectural models such as the following: various telemedicine and videoconferencing implementations and internet corporate portal architectures.

Figure 8:
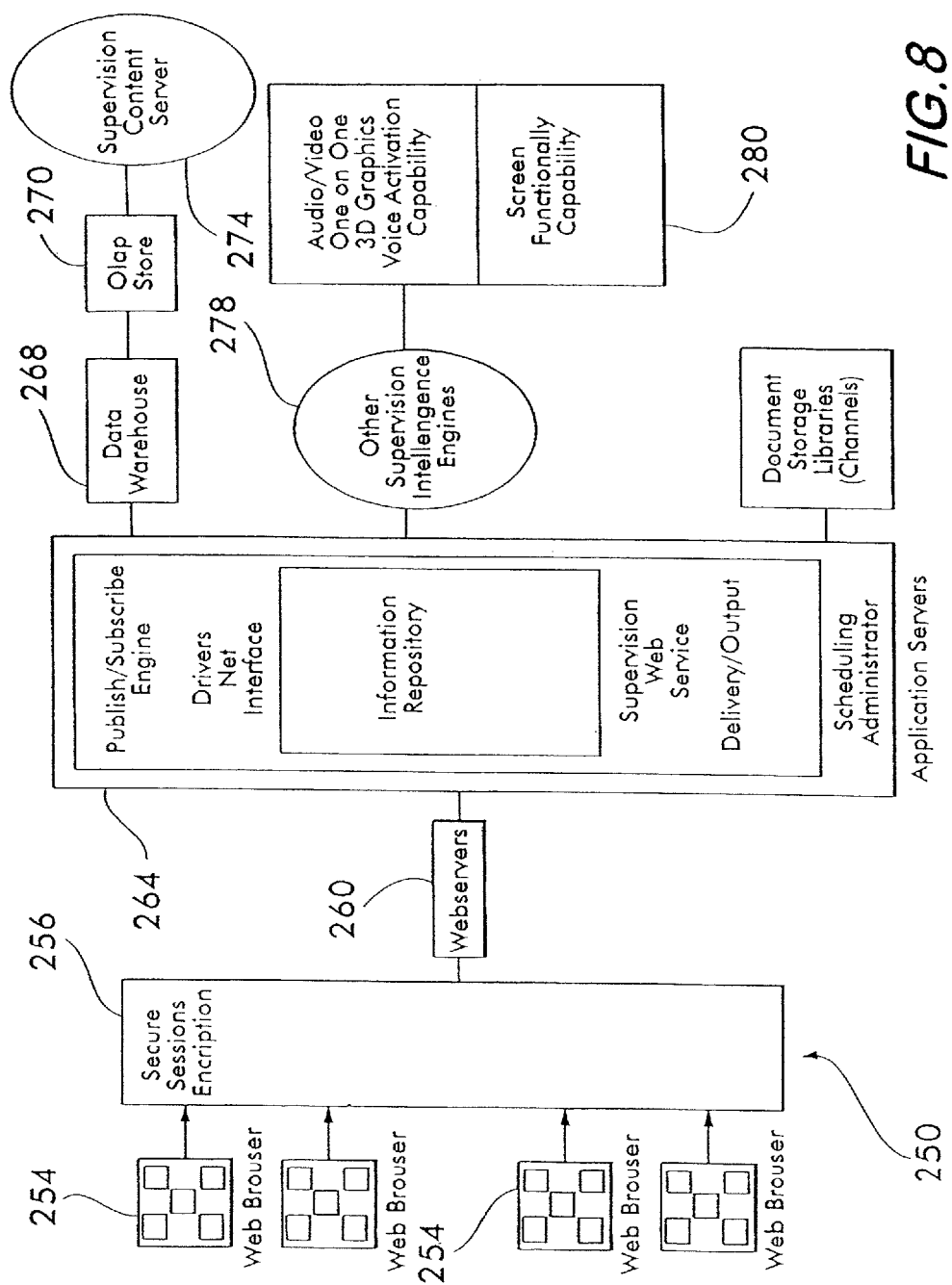
FIG. 8 shows a schematic representation of supervisory portal architecture in accordance with the present invention.

Referring now to FIG. 8, there is shown the supervision portal 250 for secure, real time interaction supervision. The supervision portal 250 can involve many of the key elements considered in the definition of an internet portal providing the functionality to support user's needs.

Any number of web browsers 254 can be coupled to the application servers 264 of the supervision portal 250 by way of the web servers 260. Brokers can be used to link the web browsers 260 to the application servers 264. In order to provide security encryption services 256 can be provided for transmitting information from the web browsers 254 to the web browsers 260.

In addition to its own information repository, the application servers 264 can have access to a data warehouse 268 and OLAP store 270 which can be coupled to the supervision content center 274. The supervision content center 274, as well as the entire supervisory web services, can be attached to any portal that may be available. Additionally, other supervision intelligence engines 278 may be provided for the application servers 264 as needed. The application servers 264 can access the audio/video, graphics and voice activation 280 by way of the supervision and intelligence engines within the applications servers 264. The screen functionality capability of the system of the present invention can also reside within block 280.

A preferred technical architecture is one wherein the following elements are considered as services and can be integrated in a comprehensive distributed object architecture. One such element is the integration of information to feed an individual's desktop computer. The preferred portal is adapted to filter the information to meet the individual's work style and content preferences, ranging from the look of the desktop to where items are displayed. Filtering and profiling capabilities are also provided. The preferred portal further provides profiling to enable the user to continuously update his or her profile based on current interest so that relevant information can be retrieved on an on going basis.

The preferred portal will permit collaboration and project style working forums for interactions among patients, doctors, lawyers, clients, suppliers, employees, customers, partners, etc. Groupware functionality can permit calendaring, project contributions, project management, work scheduling, chat, etc. It can enable participation in electronic processes through the interaction of workflow at different entry and exit points. It can also enable the publication and distribution of content creation, inclusion and distribution, thus approving what is made available to the portal through workflow processes. It can also include a search function and calendaring and event based reminders triggered by events to help manage increasing workloads, responsibilities and control processes. Finally, it can permit administration and management of the portal environment that the portal meets acceptable performance criteria, for example, time-based usage billing.

The system can include substantial document storage libraries and architecture storing supervision data, such as data directed to health related applications, integration of existing hospital, insurance, HMO, industry, government, image delivery, storage. The supervision data can also be directed to mega data systems and software data systems in a common data archive.

In operation, users accessing the services provided by the present invention can utilize web browsers such as Microsoft's Internet Explorer or Time Warner-AOL's Netscape Navigator or any other browsers known to those skilled in the art. High-speed lines are desirable but not necessary. The system can use encryption, thus offering secure sessions for patient or client confidentiality. Application servers 264 can host the information repository and the publish/subscribe engine, the crawler/filter engine and the supervision intelligence engine. The invention can offer filtered and managed access to information contained in the internet, plus proprietary data warehouses and the supervision content center 274. A supervision intelligence engine within the applications servers 264 can offer several of the unique facilities provided such as one on one audio/video, 3D visualization graphics and voice activation capability in connection with block 280. Specific screen functionalities features can also be provided. Document storage libraries can be used gather information specific to the five channels discussed above.

In substance then, the invention comprises a plurality of internet portal building tools which link to embedded, intelligent diagnostics and alerting tools. For example, artificial intelligence, neural nets, forward chaining-expert systems, technologies for structuring conferencing, records and intelligence can be provided within the internet portal architecture.

The foregoing can include multiple audio/video conferencing channels for applications such as telemedicine, one-on-one, collaborative, multi-channel applications supporting transport of audio/video with multiple audio/video and content frame windows, interactive live audio/video communication and one-on-one supervision. Such supervision can be based on industry standards combining store and forward tags with real time audio/video. Such supervision can be containing information corresponding to live motion and still images, medical instrumentation support integrating medical digital examination and vital signs from selected devices in real time. Furthermore, substantial storage capability provides access to a large volume of stored information.

The service provider, such as a health care provider or a business service provider, can have single screen access to patients/subjects while combining evaluations, monitoring virtual medical records (VMRs), diagnostic tools, pharmacology, research, statistical outcome analysis, treatment protocols, history and options, medical test results, e-commerce and content.

Figures 11, 12A:
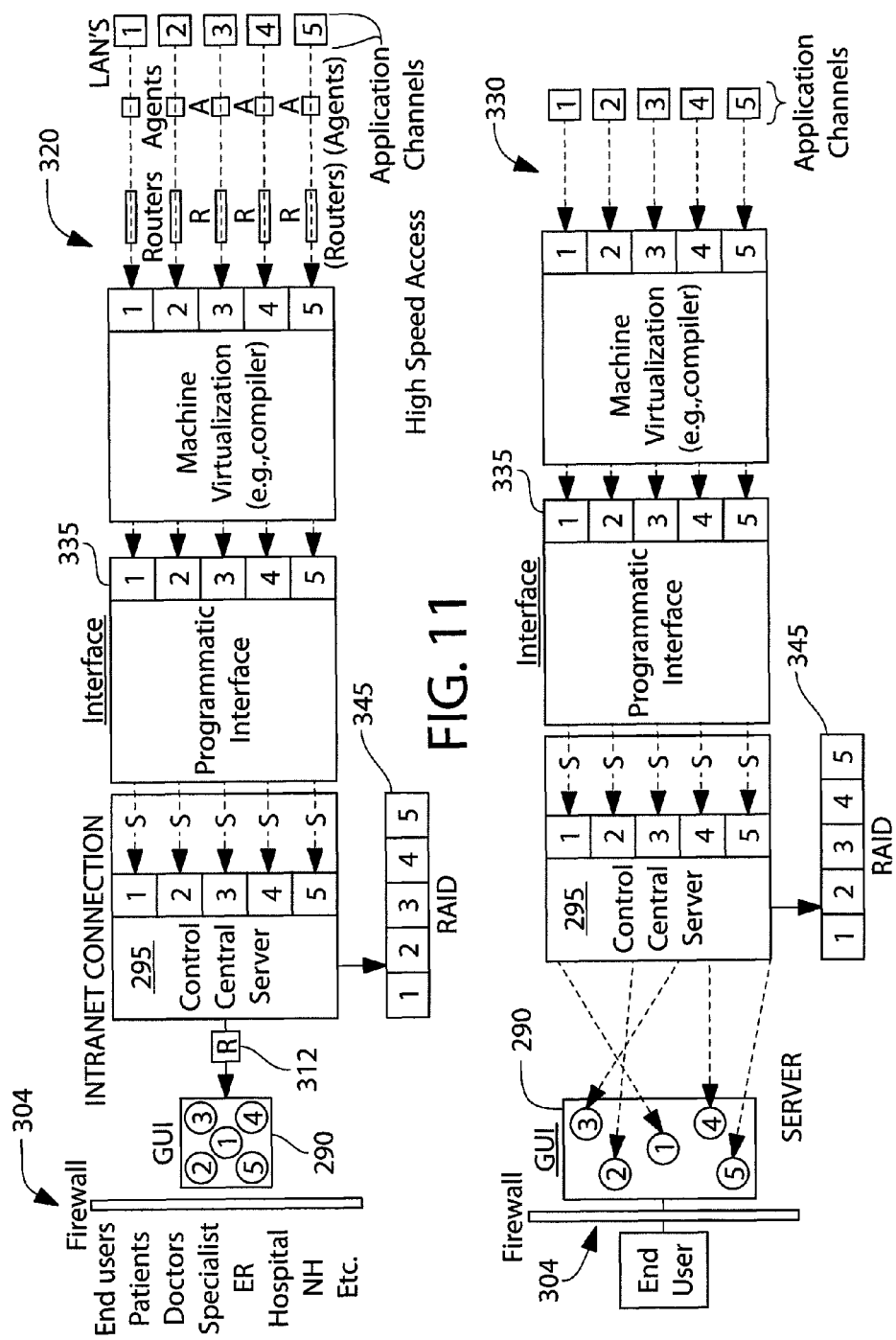
FIG. 11 shows an intranet connection which may be used with the system of the present invention.
FIGS. 12A-B show an enterprise intranet connections, including connections to a GUI, which may be used with the system of the present invention.
Figure 12B:
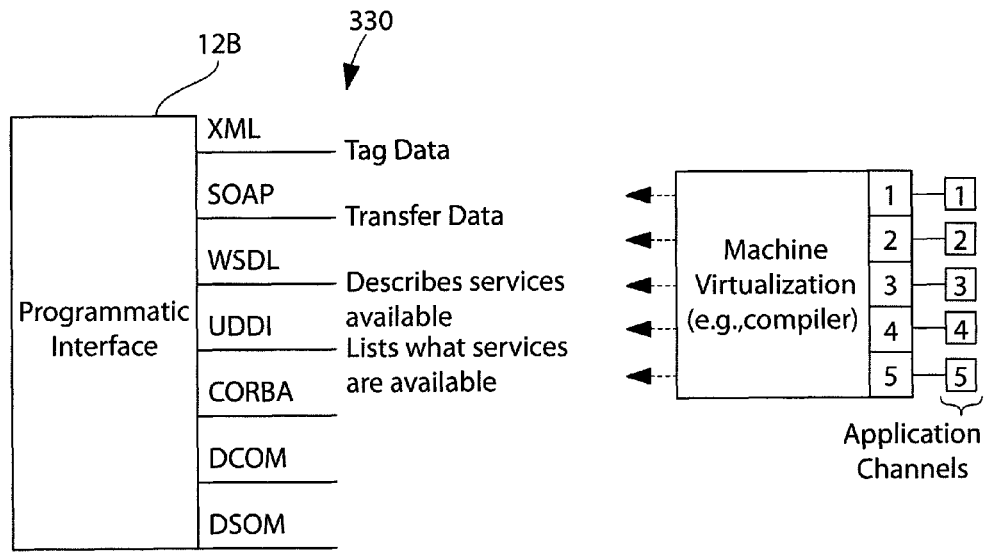

With reference to FIGS. 12A-B it can be seen that information may be structured in many ways. For example, store and forward capability can be provided. This can be accomplished using XML. Grid (spreadsheet) or record (database)-based presentation of data, comprehending quantitative, text based or static image information can also be available. Real time audio and video (low latency, high QoS threshold) based on existing and future Internet II standards are within the contemplated scope of the invention.

For example, for health-industry applications electronic medical records are the basic structure of the invention's information for storing the patient's medical history, current treatments, medications, insurance. The results of patient visits including laboratory test results, the physician's diagnosis, medications prescribed, treatments administered, the patient's billing and payment and scheduling records can be also be stored.

The abundance of information in a multi-channel environment as set forth herein can require real-time response. Thus, intelligent aids such as an alerting tool are provided. The alerting tool for real time patient monitoring can be based on knowledge systems comprising sickness symptom lists with quickly variable levels of responsiveness through fuzzy logic.

Medical annotations can be coded stored and recalled. Annotations may be voice activated and then recorded and converted to text. They can be converted to a compressed symbolic representation particularly suitable for immediate analysis for medical diagnosis and treatment.

The core portal of the present invention may be described as based on a merger of web conferencing and the web based ASP Group Ware. The invention allows service providers and end users to work together as a group, their main goal being to remotely provide services, such as health services, sharing information, such as information stored in selected EMRs, and even storing selected excerpts from audio/video interaction in EMRs. This is indeed a full Group Ware system application. The invention thus brings standardization to the medical or legal industry or to business conferencing, pulling together currently separate efforts by leading corporations and finally generating momentum.

Other attributes are useful for achieving the foregoing goals:

(1) completeness—pervasiveness of information, through multichannel audio/video availability, (2) structure—structure allowing analysis and response, through hyper annotation and linking between channels and (3) real time—real time response on that structure through diagnosis and features.

Supervision web services can require a standardized way of integrating and supervising web based services. For example, the web services can be integrated using XML, SOAP, WSDL and UDDI standards over an internet protocol backbone. XML-Tag data, SOAP-Transfer of data, WSDL-description of the services available and a UDDI-listing of the services that are available should also be provided in order to provide standardization.

Programmatic interfacing can provide the foregoing required integration of web based applications. Provision web service interfacing with private supervision internet is a preferred way to accomplish this. It would be understood that the supervision of the application of the invention interfaces services, not users. It can then add the supervision web service to a GUI such as a web page or executable program to offer specific supervision functionality. The invention supervision services will allow different applications from different sources to communicate with each other without time consuming custom programming using, in the preferred embodiment, a single password. The supervision services are not tied to any one operating system or programming language.

The API application program interface of the invention includes a set of routines, protocols and tools for building software supervision applications. This facilitates a development of a supervision program by providing all the necessary building blocks and assembling all the blocks for supervision of the teleconference. All programs can use a common API having a standard interface, thereby facilitating the operations for the end users.

An API for Microsoft's internet information server can be used as a web server. This enables programmers to develop web based supervision applications that run faster than conventional CGI programs because they are more tightly integrated with the web server. In addition to the internet information web server, any other web server from other companies than can be used.

Many of the elements required to practice the system and method of the invention are known to those skilled in the art. For example, the servlets useful for practicing the invention are known. A servlet is a small program that runs on a server. This refers to a JAVA applet that runs within a web server environment. Java applets are persistent. They remain in memory and can support multiple requests. Graphical user interfaces (GUI) make it easier to move data from one application to another. A GUI can have standard formats for representing text and graphs. Because the formats are so well defined different programs that run under a common GUI can share data. While Java can be used in a preferred embodiment, it will be understood that any programming language known to those skilled in the art can be used.

With reference to FIGS. 9 and 10, it will be understood that object orientated programming is used by programmers to define not only the data type of a data structure but also the types of operations (functions) that can be applied to the data structure. In this way the data structure becomes the object that includes both data and function. In addition programmers can create relationships between one object and another. Furthermore, they can define the channel supervision application architecture. Thus, a one on one real time audio visual interactive supervision application according to the invention can include the interactive use of virtual electronic records, devices remote monitoring and diagnostics, treatment services and administrative functionality within a multi channel seamless, secure, integrated network.

The prime focus of the network is to provide a supervision application to be used as a standard. Furthermore, the network is a supervision application for a private enterprise intranet. It can provide a standard supervision application to the internet and wireless. The network can share business logic, data and processes through a programmatic interface across a network. It can then add the supervision web service to a GUI, which can be a web page or executable program to offer supervision web services to end users. The multi channel supervision web service can enable end users to work together with ease and enable end users to participate in decisions through the supervision web service. It can also provide white board technology for ultimate supervision or consultation.

Users, alerts, annotations, maintenance and administrative are synchronized within the system of the invention. This can insure connectivity, intranet performance monitoring and management, central backup, directory services single sign on, access firewall protection and agent control. The programs of the network, which can be referred to as agents, can run in servers, switches, routers and special monitoring tools distributed in widely separated locations around intranet.

Simple network management protocol (SNMP) can set the standard for management operations and reporting. Under the SNMP each agent monitors its channels and gathers statistical information in a format management information base. Programs are polled on a regular basis for real time automatic records, inventory management, medication supplies, compliance, guidelines, chronic disease management and prevention.

Patients can be monitored at home and in affiliated hospitals with one of the multiple channels provided. Parameters that can be monitored can include weight, BP, HR, EKG, PO2 and temperature. The results can be faxed to general practitioners or specialists. Alerts can be issued by way of telephones. Remote devices in other channels can be reset on turned on and off.

Additionally, the system of the invention can share security issues still using a single sign on, GUI, servers, databases, central storage, channel supervision applications, backup, wireless network, and directories. The previously described multiple channels LAN can be integrated into the WAN intranet automatically with a single log on script.

A single log on from any computer can include authentication identification, encryption and a certification firewall to verify users to the directory server and to verify the directory server interface the end user to supervision resources automatically. A smart card can be provided for triggering a password requirement such as a facial scanning, at other locations such as pharmacy stations or localized fixed or mobile stations in the field, behind lines or in a hospital.

A unique signature key and encryption can be provided for permitting access. Key pairs in the form of a certificate can include the end users name. The certificate can contain a private key to establish authority. The certificate can pass to a directory that tracks the certified end users and their entitlements with access to specified resources. For example, a user can be entitled to some but not all of the channels.

When the agents reply within the system and method of the invention a SNMP console program can aggregate the information and present it graphically within the multiple channel supervision application format. Agents can provide content for synchronization, intelligent variable compression, browsing video environment, alerts, annotations, real time upgrades, billing, data mining, CDM and prevention.

Preferably the central server, as shown in FIG. 11, can contain storage and backup redundant equipment as well as high quality management for centralized control of the supervision web service which describes a standardized way of integrating web based applications XML, SOAP, WSDL and UDDI open standards over a intranet protocol backbone can be used. The central server programs allow LAN or channel functionality to be accessed synchronized to the patient. All end users can obtain access to the intranet through a single firewall which provides protected high speed access. A central router device routes and prioritizes traffic on a corporate intranet. LAN's are thereby linked with routers and agents. Ethernet switches can provide access to specific ports on the central server to avoid congestion. All of the devices on the WAN intranet can have a unique IP address. NAT uses special non-routable IP addresses that are reserved for a private intranet.

The network architecture of the invention can eliminate many problems. For example, latency, low bandwidth and network outages can be eliminated using the system and method of the invention. The system can communicate with as many separate systems as required. The efficiency of the system permits it to handle multiple requests at one time without being overloaded. The central control can permit intranet management and automatic updating in real time by the system and method of the invention. Cellular telephone technology can allow the system to use microwave and satellite technology. Furthermore, a hybrid system can use both wireless and wired services, e.g. the WIFI Ethernet 802.11.

Referring now to FIGS. 10A, B there are shown block diagram representations of the graphical user interface 290 and a control center server 295 that can be used with the system of the present invention. The single display of the information transmitted by way of all five channels can be made available to the end users 16, 18 simultaneously on the graphical user interface 290 to provide the supervision web services to the end users 16, 18. As shown in FIG. 10A each channel can be displayed simultaneously on a selected area of the graphical user interface 290 for viewing by the medical worker or other supervisor end user. Other end users may only receive selected ones of the five displays shown in graphical user interface 290.

The control center server 295 can be used to synchronize the information in the five channels to the particular patient which is identified to the system by the service provider or the client. This permits access to the information of all five channels with a single password for authorized end users. It serves as a direct single sign on wherein the system programs, known as agents, synthesize and synchronize the information on the five channels. This also permits annotation and storage of the information in all five channels in real time and makes the entire teleconference available for review at a later time.

Referring now to FIG. 11, there is shown a block diagram representation of an intranet connection 300 which can be used within the system and method of the present invention. In the intranet connection 300, the high speed access devices 320 include a plurality of LANs, which can have their own routers and agents for transmitting the information of the five channels to the control center server 295. A plurality of switches is provided in cooperation with the control center server 295 for performing the previously mentioned integration and synchronization of the information from the five channels of the high speed access device 320. A router 312 can route the information to any number of graphical user interfaces 290 for display to the end users 16, 18 by way of the signal firewall 304.

Referring now to FIGS. 12A-B, there are shown enterprise intranet connections 330 which may be used with the system of the present invention including the GUI 290, 295, 302 wherein the five applications channels can be mapped onto the display as shown. In the enterprise intranet connection 330 LANs are coupled to the server 295 by a programmatic interface 335, wherein the LANs are understood to represent applications being communicated by way of the application channels. This permits the supervision web service of the present invention to share business logic, data and processes through the programmatic interface 335. The supervision web service of the invention can be transmitted to the correct channel locations on the graphical user interface 290, 295, 302 as shown in the drawings by the programmatic interface 335, and displayed to the end users 16, 18 as previously described.

Figure 13:
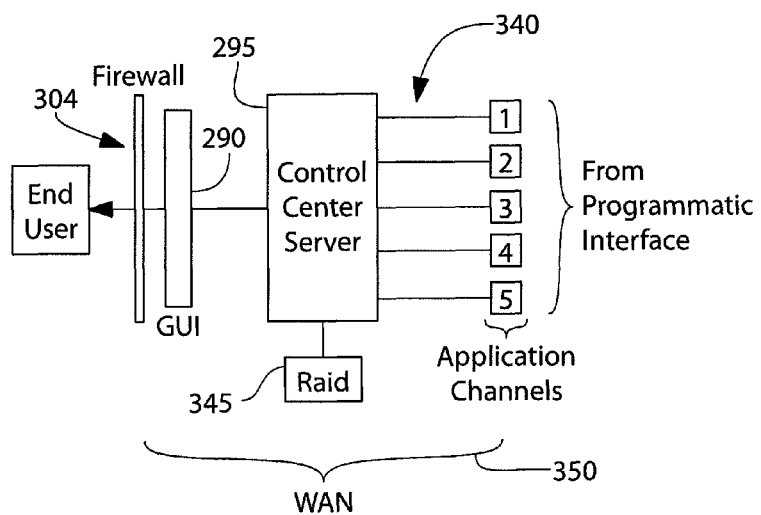
FIG. 13 shows a client-server architecture aspect which may be used with the system of the present invention.

Referring now to FIG. 13, there is shown an intranet connection 340. The intranet connection 340 permits a large integration effort for sharing the resources available in the LANs. The supervisory web services can share security issues, GUIs databases, central storage, five channel supervision, web service and applications. As previously described a backup RAID 345 can be coupled to the control center server 295 within the WAN 350.

Referring now to FIG. 14, there is shown a certificate authority process which can be used with the system and method of the present invention. In the certificate authority process 355 the end users are provided with a unique key and encryption to provide certificate 370. The directory server 380 determines whether the parties seeking access to the system are entitled to access to the requested channels. The directory server 380 can perform this operation with the authentication server 390 and the application server 400.

Thus, in one preferred embodiment of the invention the supervisory web server can: (1) work with a private enterprise intranet for supervision of web services, (2) have a control center server containing storage, backup of all channels and recording of all channels with redundant equipment for centralized control of the supervisory web service, (3) describe a standardized way of integrating web based supervision applications using XML, SOAP, WSOL, UDDI, CORBA, DCOM, DSOM open standards over an intranet protocol backbone, (4) include a central server program which serves as a programmatic interface and allows LAN or channel functionality in web based applications to be accessed and synchronized to patient, (5) permit end users to access the intranet through a single firewall which provides protected high speed access and permits one sign on only for the entire web based supervisory application, (6) include a central router device which routes and prioritizes traffic on a corporate intranet, (7) link LAN servers with routers and agents, (8) provide ethernet switching to specific ports on the control center server, (9) provide all devices with a unique IP address wherein NAT (National Address Translation) uses special non routable IP addresses that are reserved for a private intranet, (10) provide network architecture that eliminates problems such as external problems, latency, low bandwidth and network outages, (11) communicate with as many different systems as possible using any JAVA enabled machine or any other system known to those skilled in the art, (12) provide an efficient way to handle multiple requests at once without getting bogged down, (13) provide any of the five channels (supervision web based applications) desired by the end user as displayed by the GUI, (14) provide a central control center that includes intranet management, (15) automate updating in real time, (16) use cellular telephone technology with microwave and satellite telecommunication by providing hybrid bridges and wireless and wired networks, (17) use WIFI and ethernet 802 standards, (18) link through Bluetooth, (19) provide WPA (WIFI Protected Access) and (20) authenticate using TKIP (Temporal Key Integrity Protocol).

The present invention has been described with references to the enclosed figures and description. It is to be appreciated that the true spirit and scope of the invention is to be determined with reference to the attached claims.

What is claimed is:

1. A supervision network system for efficiently handling requests from multiple end users across multiple industries, the supervision network system being implemented on a private enterprise intranet over a high-speed network that includes fiber optic and wireless segments, and the supervision network system comprising:
    (I) a managed, authentication module comprising (i) an authentication server, (ii) a directory server, and (iii) an application server, wherein the authentication module is configured to:
        authenticate, using the authentication server, end users, including at least (i) supervisor end users, (ii) supervisee end users, and (iii) data-providing end users, through a certificate authority process in which the authentication server provides a public key and a private key to each end user, wherein the authentication server has a non-routable, private intranet IP address that is identifiable through a National Address Translation framework, and
        in response to receiving single sign-on requests that are initiated from wireless and wired devices belonging to end users:
            identify, using the directory server, data, from among at least five independent channels of data, to which each end user has rights to access, and
            with the application server, provide access to the identified data, wherein the single sign-on requests are received through a single firewall, and wherein the directory server has a non-routable, private intranet IP address that is identifiable through the National Address Translation framework;
    (II) a managed, machine module comprising a Java-enabled machine that is configured to communicate with multiple different systems, wherein the machine module is configured to:
        receive data from authenticated users,
        separate the data from the authenticated users into the at least five independent, managed data channels, including:
            (i) a first data channel of audio or video data,
            (ii) a second data channel of record data,
            (iii) a third data channel of real-time diagnostic data,
            (iv) a fourth data channel of treatment data, and
            (v) a fifth data channel of administrative data,
        standardize, in XML, the received data that is not already in XML, and
        provide the received data associated with the data channel that is already (i) separated into the at least five independent data channels, and (ii) in XML, to a respective intelligent router that is associated with each data channel to be routed to a respective switch associated with the data channel;
    (III) a managed, control central database module comprising (i) central application programmatic interfaces, (ii) a central server, (iii) a central database, and (iv) a redundant backup database, wherein the control central database module is configured to:
        receive, by the central application programmatic interfaces and from the switches that are associated with the data channels, the data that is (i) separated into the at least five independent data channels, and (ii) in XML, and
        store, by a central server that is associated with the central application programmatic interfaces, the data in chronological order and synchronized to the end users, both (i) in the central database and (ii) in the redundant backup database, wherein the central server has a respective non-routable, private intranet IP address that is identifiable through the National Address Translation framework;
    (IV) a network management module comprising (i) Simple Network Management Protocol (SNMP) agents and (ii) an analytics module for generating alerts and guidelines based on real-time diagnostic data indicating an abnormal condition, wherein the analytics module comprises an online analytical processing server, a data mining server, or a neural network server with forward chaining, wherein the network management module is for managing the supervision network system, including the authentication module, the machine module, the control central database module, the analytics module, and the at least first through fifth independent data channels, and wherein the network management module is configured to:
        in response to receiving one or more inputs from one or more administrator users that are monitoring the supervision network system to eliminate network problems, using statistical information exposed by the SNMP agents:
            adjust a respective right of each end user to access the data of the at least first through fifth independent data channels,
            filter the received data that is separated into the at least five independent data channels; and
    (V) a supervision graphical user interface module that is configured to output a visual representation of data that each end user has rights to access, in a respective, pre-designated user interface region that is reserved for each of the at least five independent data channels, wherein the alerts, the guidelines, and any output of the analytics module are output in the user interface region that is reserved for the fifth data channel of administrative data.

2. The supervision network system of claim 1, wherein the certificate authority process comprises a Temporal Key Integrity Protocol (TKIP) authentication process.

3. The supervision network system of claim 1, wherein the managed, machine module comprises a web services server that is configured to enforce a standardized framework for integrating and supervising web-based applications.

4. The supervision network system of claim 1, wherein the redundant backup database comprises a Redundant Array of Independent Disks (RAID).

5. A supervision method for efficiently handling requests from multiple end users across multiple industries, the supervision method being implemented on a private enterprise intranet over a high-speed, network that includes fiber optic and wireless segments, and the supervision method comprising:

authenticating, using an authentication server of a managed, authentication module that comprises (i) the authentication server, (ii) a directory server, and (iii) an application server, end users, including at least (i) supervisor end users, (ii) supervisee end users, and (iii) data-providing end users, through a certificate authority process in which the authentication server provides a public key and a private key to each end user, wherein the authentication server has a non-routable, private intranet IP address that is identifiable through a National Address Translation framework;

in response to receiving single sign-on requests that are initiated from wireless and wired devices belonging to end users:

identifying, using the directory server, data, from among at least five independent channels of data, to which each end user has rights to access, and with the application server, providing access to the identified data, wherein the single sign-on requests are received through a single firewall, and wherein the directory server has a non-routable, private intranet IP address that is identifiable through the National Address Translation framework;

receiving, using a managed, machine module comprising a Java-enabled machine that is configured to communicate with multiple different systems, data from authenticated users;

separating, using the managed, machine module, the data from the authenticated users into the at least five independent, managed data channels, including:
(i) a first data channel of audio or video data,
(ii) a second data channel of record data,
(iii) a third data channel of real-time diagnostic data,
(iv) a fourth data channel of treatment data, and
(v) a fifth data channel of administrative data;

standardizing, using the managed, machine module, and in XML, the received data that is not already in XML;

providing, using the managed, machine module, the received data associated with the data channel that is already (i) separated into the at least five independent data channels, and (ii) in XML, to a respective intelligent router that is associated with each data channel to be routed to a respective switch associated with the data channel;

receiving, by central application programmatic interfaces of a managed, control central database module that comprises (i) the central application programmatic interfaces, (ii) a central server, (iii) a central database, and (iv) a redundant backup database, and from the switches that are associated with the data channels, the data that is (i) separated into the at least five independent data channels, and (ii) in XML;

storing, by the central server that is associated with the central application programmatic interfaces, the data in chronological order and synchronized to the end users, both (i) in the central database and (ii) in the redundant backup database, wherein the central server has a respective non-routable, private intranet IP address that is identifiable through the National Address Translation framework in response to receiving one or more inputs from one or more administrator users that are monitoring the supervision network system to eliminate network problems, using statistical information exposed by the SNMP agents:

adjust, by a network management module that comprises (i) Simple Network Management Protocol (SNMP) agents and (ii) an analytics module for generating alerts and guidelines based on real-time diagnostic data indicating an abnormal condition, a respective right of each end user to access the data of the at least first through fifth independent data channels, wherein the analytics module comprises an online analytical processing server, a data mining server, or a neural network server with forward chaining, wherein the network management module is for managing the authentication module, the machine module, the control central database module, the analytics module, and the at least first through fifth independent data channels a respective right of each end user to access the data of the at least first through fifth independent data channels, filter, by the network management module, the received data that is separated into the at least five independent data channels; and outputting, using a supervision graphical user interface module that is configured to a visual representation of data that each end user has rights to access, in a respective, pre-designated user interface region that is reserved for each of the at least five independent data channels, wherein the alerts, the guidelines, and any output of the analytics module are output in the user interface region that is reserved for the fifth data channel of administrative data.

6. The supervision method of claim 5, wherein the certificate authority process comprises a Temporal Key Integrity Protocol (TKIP) authentication process.

7. The supervision method of claim 5, wherein the managed, machine module comprises a web services server that is configured to enforce a standardized framework for integrating and supervising web-based services.

8. The supervision method of claim 5, wherein the redundant backup database comprises a Redundant Array of Independent Disks (RAID).

9. A computer readable non-transitory storage medium storing instructions executable by one or more computers which, upon such execution, cause the one or more computers to perform operations for efficiently handling requests from multiple end users across multiple industries, the supervision operations being implemented on a private enterprise intranet over a high-speed, network that includes fiber optic and wireless segments, and the operations comprising:

authenticating, using an authentication server of a managed, authentication module that comprises (i) the authentication server, (ii) a directory server, and (iii) an application server, end users, including at least (i) supervisor end users, (ii) supervisee end users, and (iii) data-providing end users, through a certificate authority process in which the authentication server provides a public key and a private key to each end user, wherein the authentication server has a non-routable, private intranet IP address that is identifiable through a National Address Translation framework;

in response to receiving single sign-on requests that are initiated from wireless and wired devices belonging to end users:
  identifying, using the directory server, data, from among at least five independent channels of data, to which each end user has rights to access, and
  with the application server, providing access to the identified data, wherein the single sign-on requests are received through a single firewall, and wherein the directory server has a non-routable, private intranet IP address that is identifiable through the National Address Translation framework;
receiving, using a managed, machine module comprising a Java-enabled machine that is configured to communicate with multiple different systems, data from authenticated users;
separating, using the managed, machine module, the data from the authenticated users into the at least five independent, managed data channels, including:
  (i) a first data channel of audio or video data,
  (ii) a second data channel of record data,
  (iii) a third data channel of real-time diagnostic data,
  (iv) a fourth data channel of treatment data, and
  (v) a fifth data channel of administrative data;
standardizing, using the managed, machine module, and in XML, the received data that is not already in XML;
providing, using the managed, machine module, the received data associated with the data channel that is already (i) separated into the at least five independent data channels, and (ii) in XML, to a respective intelligent router that is associated with each data channel to be routed to a respective switch associated with the data channel;
receiving, by central application programmatic interfaces of a managed, control central database module that comprises (i) the central application programmatic interfaces, (ii) a central server, (iii) a central database, and (iv) a redundant backup database, and from the switches that are associated with the data channels, the data that is (i) separated into the at least five independent data channels, and (ii) in XML;
storing, by the central server that is associated with the central application programmatic interfaces, the data in chronological order and synchronized to the end users, both (i) in the central database and (ii) in the redundant backup database, wherein the central server has a respective non-routable, private intranet IP address that is identifiable through the National Address Translation framework
in response to receiving one or more inputs from one or more administrator users that are monitoring the supervision network system to eliminate network problems, using statistical information exposed by the SNMP agents:
  adjust, by a network management module that comprises (i) Simple Network Management Protocol (SNMP) agents and (ii) an analytics module for generating alerts and guidelines based on real-time diagnostic data indicating an abnormal condition, a respective right of each end user to access the data of the at least first through fifth independent data channels, wherein the analytics module comprises an online analytical processing server, a data mining server, or a neural network server with forward chaining, wherein the network management module is for managing the authentication module, the machine module, the control central database module, the analytics module, and the at least first through fifth independent data channels a respective right of each end user to access the data of the at least first through fifth independent data channels,
  filter, by the network management module, the received data that is separated into the at least five independent data channels; and
outputting, using a supervision graphical user interface module that is configured to a visual representation of data that each end user has rights to access, in a respective, pre-designated user interface region that is reserved for each of the at least five independent data channels, wherein the alerts, the guidelines, and any output of the analytics module are output in the user interface region that is reserved for the fifth data channel of administrative data.

10. The medium of claim 9, wherein the certificate authority process comprises a Temporal Key Integrity Protocol (TKIP) authentication process.

11. The medium of claim 9, wherein the managed, machine module comprises a web services server that is configured to enforce a standardized framework for integrating and supervising web-based services.

12. The medium of claim 9, wherein the redundant backup database comprises a Redundant Array of Independent Disks (RAID).

* * * * *